United States Patent [19]

Venuti

[11] Patent Number: 4,786,652
[45] Date of Patent: Nov. 22, 1988

[54] NAPHTHALENE ANTI-PSORIATIC AGENTS

[75] Inventor: Michael C. Venuti, San Francisco, Calif.

[73] Assignee: Syntex (U.S.A.) Inc., Palo Alto, Calif.

[21] Appl. No.: 23,591

[22] Filed: Mar. 9, 1987

[51] Int. Cl.[4] .................. A61K 31/27; A61K 31/265; C07C 69/96; C07C 125/075
[52] U.S. Cl. ..................................... 514/481; 514/510; 514/863; 558/266; 558/268; 560/29; 560/31; 560/32; 560/115; 560/134; 260/396 R
[58] Field of Search ............... 558/268, 266; 560/134, 560/29, 31, 32; 514/481, 863, 510

[56] References Cited

U.S. PATENT DOCUMENTS

| 2,383,392 | 8/1945  | Karrer        | 260/139    |
| 3,935,267 | 1/1976  | Hauck et al.  |            |
| 3,958,006 | 5/1976  | Payne         | 514/481    |
| 4,181,741 | 1/1980  | Bullock       | 558/268 X  |
| 4,229,478 | 10/1980 | Jones et al.  | 514/520 X  |
| 4,466,981 | 8/1984  | Jones et al.  | 560/139 X  |
| 4,593,120 | 6/1986  | Jones et al.  | 560/107    |

FOREIGN PATENT DOCUMENTS 0150831 8/1985 European Pat. Off. .

OTHER PUBLICATIONS

*Alkoxy Exchange Reactions of Naphthalene Ethers*, by J. E. Baldwin, et al. Journal of Organic Chemistry, vol. 34, 2788-2790.

*Primary Examiner*—Vivian Garner
*Attorney, Agent, or Firm*—Brian Lewis; Annette Moore; Tom M. Moran

[57] ABSTRACT

Psoriasis in mammals is relieved by topically administering naphthalenes of the formula:

(I)

[Structure: naphthalene with OX at position 1, $R^1$ at position 2, $R^2$ at position 3, OX at position 4, and $(R^3)_m$ on the other ring]

wherein:

$R^1$ is lower alkoxy or optionally substituted phenoxy, $R^2$ is the same as $R^1$, or $R^2$ is hydrogen, lower alkyl, optionally substituted phenyl or optionally substituted phenylalkyl, $R^3$ is hydrogen, lower alkyl, lower alkoxy, halo, optionally substituted phenyl, optionally substituted phenyl-lower-alkyl or optionally substituted phenyl-lower-alkoxy, and m is 1 or 2;

X is the same and is either $-C(O)OR^4$ or $-C(O)NR^5R^6$, wherein $R^4$ is alkyl, phenyl or benzyl optionally substituted with one or two lower alkyl groups, lower alkoxy groups or halo; and $R^5$ and $R^6$ are independently hydrogen, lower alkyl, cycloalkyl or phenyl optionally substituted with one or two lower alkyl groups, lower alkoxy groups or halo.

36 Claims, No Drawings

NAPHTHALENE ANTI-PSORIATIC AGENTS

BACKGROUND OF THE INVENTION

1. Field of the Invention

The invention relates to naphthalene derivatives which are useful in inhibiting certain dermatological conditions and inhibiting lipoxygenase activity, particularly 5-lipoxygenase activity which makes the compounds useful for topical treatment of inflammatory states. This invention also relates to pharmaceutical compositions useful in relieving the effects of certain chronic recurrent papulosquamous dermatoses, e.g., psoriasis. This invention also relates to a process for preparing compounds of this invention.

2. Related Disclosures

Psoriasis is a skin disease characterized in part by excessive proliferation of cells of the epidermis which remain strongly adherent and build up into a scaley plaque typical of the disease. While currently available therapies, such as corticosteroids, vitamin A derivatives (retinoids), cancer chemotherapeutic agents (methotrexate, razoxane), coal tar and anthralin preparations, and psoralen-u.v. irradiation (PUVA) are effective in controlling the disease to a certain extent, they can cause numerous and sometimes severe undesirable side effects including renal irritation, hepatic toxicity, and erythema.

Certain naphthoquinone derivatives are known to be useful in treating psoriasis. See, for example, U.S. Pat. Nos. 4,229,478, 4,466,981 and 4,593,120 and British Pat. No. 1,243,401. Carbamate and carbonate derivatives of naphthalene having insecticidal properties are known. See, for example, U.S. Pat. Nos. 2,383,392, 3,958,006 and 4,181,741. Surprisingly, it has been discovered that the compounds of the instant invention are also effective antipsoriatic agents. The compounds of the present invention are more stable in the topical formulations normally used.

SUMMARY

The present invention relates to a compound of the formula

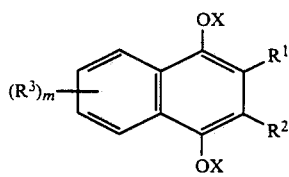

wherein:

$R^1$ is lower alkoxy of one to six carbon atoms or phenoxy optionally substituted by one or two substituents chosen from lower alkyl of one to four carbon atoms, lower alkoxy of one to four carbon atoms and halo;

$R^2$ is the same as $R^1$, or $R^2$ is hydrogen, lower alkyl of one to six carbon atoms, phenyl or phenyl-lower-alkyl, wherein the phenyl ring of the phenyl or phenyl-lower-alkyl group is optionally substituted by one or two substituents chosen from lower alkyl of one to four carbon atoms, lower alkoxy of one to four carbon atoms and halo;

$R^3$ is hydrogen, halo, lower alkyl of one to six carbon atoms, lower alkoxy of one to six carbon atoms, phenyl, phenyl-lower-alkyl or phenyl-lower-alkoxy, wherein the phenyl ring of the phenyl, phenyl-lower-alkyl or phenyl-lower-alkoxy group is optionally substituted by one or two substituents chosen from lower alkyl of one to four carbon atoms, lower alkoxy of one to four carbon atoms and halo;

m is 1 or 2; and

X is the same and is either $-C(O)OR^4$ or $-C(O)NR^5R^6$, wherein $R^4$ is alkyl of one to seven carbon atoms, phenyl or benzyl, wherein the phenyl ring of the phenyl or benzyl group is optionally substituted by one or two substituents chosen from lower alkyl of one to four carbon atoms, lower alkoxy of one to four carbon atoms and halo; and $R^5$ and $R^6$ are independently hydrogen, lower alkyl of one to six carbon atoms, cycloalkyl of five to eight carbon atoms or phenyl optionally substituted with one or two substituents chosen from lower alkyl of one to four carbon atoms, lower alkoxy of one to four carbon atoms and halo.

Another aspect of the invention is a pharmaceutical composition is a form suitable for topical administration to mammals comprising a compound of formula (I) and a pharmaceutically acceptable excipient.

Another aspect of the invention is a method for relieving inflammatory diseases such as the condition of psoriasis in a mammal which comprises topically administering to said mammal a psoriasis-relieving amount of a compound of formula (I).

DETAILED DESCRIPTION AND PREFERRED EMBODIMENT

In its broadest aspect, the present invention relates to compounds of the formula

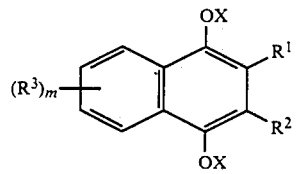

wherein:

$R^1$ is lower alkoxy of one to six carbon atoms or phenoxy optionally substituted by one or two substituents chosen from lower alkyl of one to four carbon atoms, lower alkoxy of one to four carbon atoms and halo;

$R^2$ is the same as $R^1$, or $R^2$ is hydrogen, lower alkyl of one to six carbon atoms, phenyl or phenyl-lower-alkyl, wherein the phenyl ring of the phenyl or phenyl-lower-alkyl group is optionally substituted by one or two substituents chosen from lower alkyl of one to four carbon atoms, lower alkoxy of one to four carbon atoms and halo;

$R^3$ is hydrogen, halo, lower alkyl of one to six carbon atoms, lower alkoxy of one to six carbon atoms, phenyl, phenyl-lower-alkyl or phenyl-lower-alkoxy, wherein the phenyl ring of the phenyl, phenyl-lower-alkyl or phenyl-lower-alkoxy group is optionally substituted by one or two substituents chosen from lower alkyl of one to four carbon atoms, lower alkoxy of one to four carbon atoms and halo;

m is 1 or 2; and

X is the same and is either $-C(O)OR^4$ or $-C(O)NR^5R^6$, wherein $R^4$ is alkyl of one to seven carbon atoms, pheny or benzyl, wherein the phenyl ring of the phenyl or benzyl group is optionally substituted by one or two substituents chosen from lower alkyl of one to four carbon atoms, lower alkoxy of one to four carbon atoms and halo; and $R^5$ and $R^6$ are independently hydrogen, lower alkyl of one to six carbon atoms, cycloalkyl of five to eight carbon atoms or phenyl optionally substituted with one or two substituents chosen from lower alkyl of one to four carbon atoms, lower alkoxy of one to four carbon atoms and halo.

The compounds of formula (I) may be divided into subgroups (Ia) and (Ib).

Compounds of subgroup (Ia) are represented by formula (I) wherein X is —C(O)NR$^5$R$^6$ wherein $R^5$ and $R^6$ are as defined above. Within this subgroup it is preferred that $R^1$ is methoxy or ethoxy, $R^2$ is methoxy, ethoxy, hydrogen or methyl, $R^5$ is hydrogen and $R^6$ is methyl or ethyl, with $R^1$ and $R^2$ being methoxy being the most preferred.

Compounds of subgroup (Ib) are represented by formula (I) wherein X is —C(O)OR$^4$ wherein $R^4$ is as defined above. Within this subgroup it is preferred that $R^1$ is methoxy or ethoxy, $R^2$ is methoxy, ethoxy, hydrogen or methyl and $R^4$ is methyl or ethyl, with $R^1$ and $R^2$ being methoxy being the most preferred.

An even more specific embodiment of the instant invention are compounds of formula (I) wherein m is 1 and $R^3$ is at the 6-position and is bromo, chloro, fluoro, methoxy, ethoxy, n-propoxy, i-propoxy, n-butoxy, and i-butoxy, with chloro being preferred.

A preferred embodiment of the invention are compounds of formula (I) wherein $R^3$ is hydrogen.

Another embodiment of the invention are compounds wherein m is 2 and the two $R^3$ groups are at the 6 and 7 positions and are lower alkyl, lower alkoxy or halo with $R^3$ being methyl being preferred.

In the present specification and claims the term "alkyl" is intended to mean alkyl groups containing one to seven carbon atoms including straight chain groups, or branched chain groups. Illustrative of such groups are for example, methyl, ethyl, n-propyl, i-propyl, n-hexyl, 2-methylpentyl, n-heptyl, 2,2-dimethylbutyl and 3,3-dimethylpentyl. The term "lower alkyl" refers to alkyl groups of one to six carbo atoms as defined above. Examples of "lower alkyl" groups are methyl, ethyl, n-propyl, i-propyl, n-butyl, i-butyl, s-butyl, 2,2-dimethylpropyl and t-hexyl. The term "phenyl-lower-alkyl" refers to an optionally substituted phenyl ring attached to an alkylene chain of one to six carbon atoms.

The term "lower alkoxy" refers to a straight or branched chain aliphatic group of one to six carbon atoms having bonded thereto an oxygen moiety. Examples of "lower alkoxy" are methoxy, ethoxy, n-propoxy, i-propoxy, n-butoxy, i-butoxy, s-butoxy, t-butoxy and n-pentyloxy. "Phenyl-lower-alkoxy" refers to a phenyl ring attached to an alkylene chain of one to six carbon atoms having bonded thereto an oxygen atom. Examples of "phenyl-lower-alkoxy" are benzyloxy, 4-chlorophenylethoxy, phenyl-n-propoxy and 2-methoxyphenyl-n-hexyloxy.

The term "sterically hindered" refers to alkyl groups wherein branching occurs at the carbon adjacent to or one carbon removed from the carbonyl group or to optionally substituted phenyl.

Optionally substituted phenyl refers to a phenyl ring optionally substituted by one or more substituents selected from the group consisting of lower alkyl, lower alkoxy and halo unless otherwise defined.

The term "halo" refers to fluoro, chloro, and bromo.

It is possible that the preparation of compounds of formula (II) where both $R^2$ and $R^3$ are other than hydrogen may give rise to a mixture of two isomers, i.e. the two isomers where $R^2$ is at the 2- or the 3-position of the compound of formula (II). Without separation, this would lead eventually to a mixture of 2- and 3-isomers of the compound of formula (I). In the event that such a mixture is obtained, the isomers may be separated by crystallization, normal or reverse phase HPLC or other partition chromatographic techniques, and the like. The claims and specification of this patent application are intended to encompass each individual isomer of formula (I) alone or in combination with its corresponding isomer, unless specifically designated otherwise.

FORMULATION AND ADMINISTRATION

The compositions of the present invention may be formulated for administration in any convenient way by analogy with other topical compositions adapted for use in mammals. These compositions may be presented for use in any conventional manner with the aid of any of a wide variety of pharmaceutical carriers or vehicles.

The naphthalenes of formula (I) may be formulated with suitable pharmaceutical vehicles known in the art to form particularly effective topical compositions. An effective amount of the naphthalene compound is about 0.001%w to about 10%w of the total formulated composition. The rest of the formulated composition will be about 90%w to about 99.999%w of a suitable excipient which may include a pharmaceutically acceptable solvent and other pharmaceutically acceptable additives to form a topically effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, aerosols, solutions and the like. Particularly suitable solvents include water, ethanol, acetone, glycerine, propylene carbonate, dimethylsulfoxide (DMSO), and glycols such as 1,2-propylene diol, i.e., propylene glycol, 1,3-propylene diol, polyethylene glycol having a molecular weight of from 100 to 10,000, dipropylene glycol, etc. and mixtures of the aforementioned solvents with each other.

A topical cream may be prepared as a semi-solid emulsion of oil in water or water in oil. A cream base formulation by definition is an emulsion, which is a two-phase system with one liquid (for example fats or oils) being dispersed as small globules in another substance (e.g., a glycol-water solvent phase) which may be employed as the primary solvent for the naphthalenes therein. The cream formulation may contain fatty alcohols, surfactants, mineral oil or petrolatum and other typical pharmaceutical adjuvants such as anti-oxidants, antiseptics, or compatible adjuvants. A typical cream base formulation is as follows:

| | |
|---|---|
| Water/glycol mixture (15% or more glycol) | 50-99 parts by weight |
| Fatty Alcohol | 1-20 |
| Non-ionic Surfactant | 0-10 |
| Mineral Oil | 0-10 |
| Typical Pharmaceutical Adjuvants | 0-5 |

| | |
|---|---|
| -continued | |
| Active Ingredients | 0.001-10 |

The fatty alcohol, non-ionic surfactant, and other adjuvants are discussed in U.S. Pat. No. 3,934,013 to Poulsen which is incorporated herein by reference.

The naphthalenes of formula (I) may also be formulated as topical ointments. A "classical" ointment is a semisolid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

| | |
|---|---|
| White Petrolatum | 40-94 parts by weight |
| Mineral Oil | 5-20 |
| Glycol Solvent | 1-15 |
| Surfactant | 0-10 |
| Stabilizer | 0-10 |
| Active Ingredients | 0.001-10.0 |

Other suitable ointment base formulations which employ propylene carbonate are described in U.S. Pat. No. 4,017,615 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much of those applications as is pertinent is incorporated herein by reference. Following is a typical ointment base formulation containing propylene carbonate:

| | |
|---|---|
| Active Ingredients | 0.001-10.0 parts by weight |
| Propylene Carbonate | 1-10 |
| Solvent | 1-10 |
| Surfactant | 0-10 |
| White Petrolatum | 70-97 |

Suitable solvents, surfactants, stabilizers, etc. are discussed in U.S. Pat. No. 3,934,013 and such are incorporated herein by reference.

A suitable topical "non-classical" anhydrous, water washable "ointment type" base is described in U.S. Pat. No. 3,592,930 to Kats and Neiman, and that patent is incorporated herein by reference. A representative composition of this invention utilizing such base is as follows:

| | |
|---|---|
| Glycol Solvent | 40-35 parts by weight |
| Fatty Alcohol | 15-45 |
| Compatible Plasticizer | 0-15 |
| Compatible Coupling Agent | 0-15 |
| Penetrant | 0-20 |
| Active Ingredients | 0.001-10.0 |

Another aspect of the invention is a method for relieving the condition of psoriasis in a mammal by topically administering a composition containing a compound of formula (I) wherein $R^1$, $R^2$, $R^3$, $R^4$, $R^5$, $R^6$, X and m are as defined above. Generally, the anti-psoriatic manifestation in mammals, particularly humans, is combatted by contacting the inflamed areas with a therapeutically effective amount of the naphthalene-containing compositions of this invention, that is, an amount which results in a lessening of the epidermal cell proliferation (an anti-psoriatic effect). Preferably the naphthalenes are first formulated to prepare a suitable pharmaceutical formulation, as discussed hereinabove, which is then placed in contact with the afflicted area(s). An effective amount of the naphthalene compound will depend upon the particular condition and the mammal receiving the treatment and will vary between 0.001% to 10% by weight of the pharmaceutical composition and preferably will be between 0.01% and 1% by weight of the formulation. Using these levels in the formulation, a therapeutically effective and non-side effect producing amount, i.e. enough to affect an anti-psoriatic response, but not enough to adversely effect the recipient, is applied to the afflicted area(s).

The compounds of this invention are also useful for treating mammals having a variety of disease states caused by lipoxygenase activity, particularly 5-lipoxygenase activity.

In vitro lipoxygenase inhibiting activity of the compounds of this invention are determined by the standard Human Polymorphonuclear Leukocytes assay. This assay is a modification of that described by O. Radmark, C. Malmsten, and B. Samuelsson in *FEBS Letter*, 110, 213-215, 1980. In vivo lipoxygenase inhibiting activity of the comounds of this invention are determined by the arachidonic acid mouse ear inflammation assay as described by J. M. Young, D. A. Spires, C. J. Bedord, B. Wagner, S. J. Ballaron and L. M. DeYoung in *Journal of Investigative Dermatology*, 82, 367-371, 1984.

PREPARATION

The compounds of formula (I) where $R^1$ and $R^2$ are the same and are lower alkoxy or optionally substituted phenoxy may be prepared from intermediates of formula (V), (where $R^1$ and $R^2$ are as defined above), the preparation of which is shown below in Reaction Sequence I.

REACTION SEQUENCE I

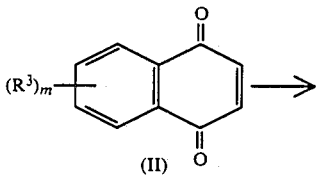

(II)

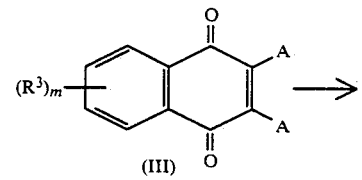

(III)

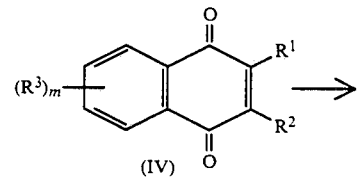

(IV)

-continued
REACTION SEQUENCE I

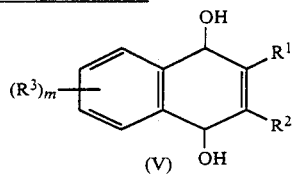

wherein $R^1$ and $R^2$ are the same and are lower alkoxy or optionally substituted phenoxy, A is chlorine or bromine and $R^3$ is as defined above.

The intermediates of formula (II), where $R^2$ is hydrogen and $R^3$ is as defined above, are prepared according to the method disclosed in J. Am. Chem. Soc., 70, 3165 (1948) and Ibid., 71, 3615 (1949). A butadiene substituted with the appropriate embodiment of $R^3$ is reacted with 1,4-benzoquinone in a solvent such as acetic acid at a temperature of −10° C. to 30° C., preferably at 25° C. for 24 to 72 hours, preferably from 40 to 48 hours. The 5,8-dihydro derivative of the compound of formula (II) is recovered and treated with an oxidizing agent such as sodium dichromate, sodium nitrite, manganese dioxide and the like to form compounds of formula (II) where $R^2$ is hydrogen.

Compounds of formula (III) are prepared by reacting the compound of formula (II) with chlorine or bromine, preferably chlorine. For example, chlorine gas is bubbled into a solution of the compound of formula (II) dissolved in a solvent such as glacial acetic acid, nitrobenzene, carbon tetrachloride and the like, preferably glacial acetic acid at reflux temperature in the presence of a suitable catalyst such as sodium acetate, iodine, iron(III)chloride, dimethylformamide or lower alcohols, for example methanol or ethanol, preferably about 0.1 molar equivalent of iodine. The compound of formula (III) where $R^3$ is hydrogen and A is chlorine is commercially available from, i.a., Aldrich Chemical Co..

Compounds of formula (IV) are prepared from the 2,3-dihalonaphthoquinone of formula (III), preferably a 2,3-dichloro-1,4-naphthoquinone. The compound of formula (III) is reacted with an alkali metal alkoxide or phenoxide of formula $R^1M$, where M is an alkali metal. The reaction is conducted in an inert organic solvent such as tetrahydrofuran, dimethylsulfoxide, dimethylformamide and the like, or preferably in an alcohol of formula $R^1H$, at temperatures from about 20° C. to about 100° C., preferably about 60°–70° C., for a time sufficient to assure completeness of reaction, i.e., for about 30 minutes to about 8 hours, preferably about 1–2 hours. When the reaction is substantially complete the compound of formula (IV), where $R^1$ and $R^2$ are the same, is isolated by conventional means, such as crystallization.

Compounds of formula (IV) are then reduced to compounds of formula (V). The compound of formula (IV) may be hydrogenated in a hydrogen atmosphere in the presence of a catalyst such as palladium on charcoal, or alternatively reduced using transfer hydrogenation conditions with, for example, cyclohexadiene and a catalyst such as palladium on charcoal. Polar solvents such as tetrahydrofuran, dimethylformamide or ethanol are preferred, most preferably tetrahydrofuran. Alternatively, the compounds of formula (IV) are reduced with sodium hydrosulfite in an alcoholic solvent, for example methanol or ethanol, to give the compound of formula (V) where $R^1$ and $R^2$ are the same and are lower alkoxy or optionally substituted phenoxy.

The compounds of formula (I) where $R^1$ is lower alkoxy or optionally substituted phenoxy, and $R^2$ is hydrogen, lower alkyl, optionally substituted phenyl or optionally substituted phenylalkyl may be prepared from intermediates of formula (V), (where $R^1$ and $R^2$ are as defined above), the preparation of which is shown below in Reaction Sequence II.

REACTION SEQUENCE II

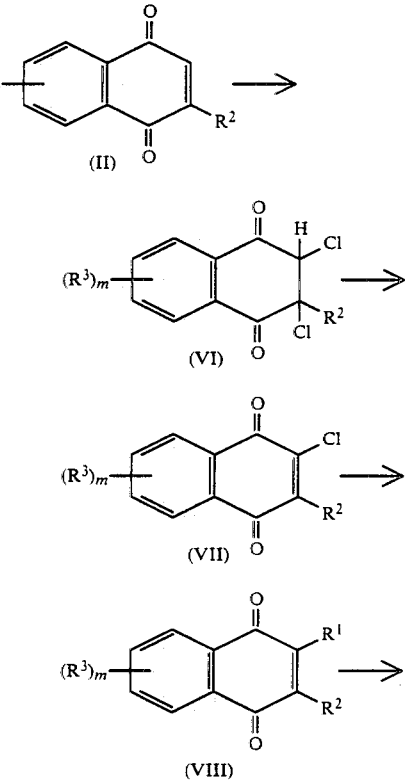

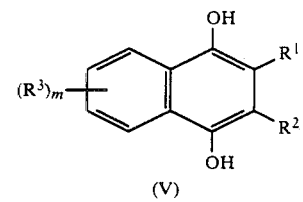

The intermediates of formula (II), where $R^2$ is hydrogen and $R^3$ is as defined above are prepared according to the method disclosed in Reaction Sequence I, supra. Compounds of formula (II) wherein $R^2$ is alkyl, optionally substituted phenyl or phenylalkyl may be prepared by reacting the naphthoquinone of formula (II) wherein $R^2$ is hydrogen with an acid of the formula $R^2COOH$ wherein $R^2$ is as defined above but is other than hydrogen. A solution of the acid and naphthoquinone in acetonitrile and sulfolane in the presence of a metal nitrate, e.g. silver nitrate and the like, is heated to 50°–100° C., preferably to 55°–75° C. A solution of a persulfate salt, e.g. diammonium persulfate, is added dropwise. Compounds of formula (II) wherein $R^2$ is alkyl, optionally substituted phenyl or phenylalkyl are recovered by conventional means such as chromatography.

Compounds of formula (VI) are prepared by bubbling chlorine gas into a solution of compound of formula (II) dissolved in a solvent such as glacial acetic acid, nitrobenzene, carbon tetrachloride and the like, preferably glacial acetic acid maintained at about 15° C. The compound of formula (VI), which may be isolated by known means, dissolved in a solvent such as acetic acid is treated with a suitable catalyst such as sodium acetate, iodine, iron(III)chloride, dimethylformamide or lower alcohols, for example methanol or ethanol, with heating under reflux for ½ to 4 hours, preferably for 1 to 2½ hours to yield compounds of formula (VII).

Compounds of formula (VIII) are prepared by reacting compound of formula (VII) with an alkali metal alkoxide or phenoxide such as sodium alkoxide or phenoxide, e.g. sodium methoxide or phenoxide in an anhydrous solvent such as methanol, dimethylformamide, tetrahydrofuran and the like, the solvent if an alcohol being chosen according to the length of the alkyl chain on the alkoxy group e.g. sodium methoxide in methanol, sodium ethoxide in ethanol and the like. The reaction mixture is stirred at a temperature of about 0° C. to 60° C., preferably about 25° C., for about 3 hours to 24 hours, preferably for about 10 to 18 hours. Compounds of formula (VIII) are recovered by conventional means such as by crystallization.

Compounds of formula (VII) may also be converted to compounds of formula (VIII), by treatment with an alcoholic solution of a strong base such as potassium hydroxide in methanol and then alkylating the intermediate compound of formula (X), infra, using the appropriate halide or an alcohol as is described hereinafter under Reaction Sequence III.

Compounds of formula (VIII) are then reduced to compounds of formula (V). The compound of formula (VIII) may be hydrogenated in a hydrogen atmosphere in the presence of a catalyst such as palladium on charcoal, or alternatively reduced using transfer hydrogenation conditions with, for example, cyclohexadiene and a catalyst such as palladium on charcoal. Polar solvents such as tetrahydrofuran, dimethylformamide or ethanol are preferred, most preferably tetrahydrofuran. Alternatively, the compounds of formula (VIII) are reduced with sodium hydrosulfite in an alcoholic solvent, for example methanol or ethanol. Thus the compounds of formula (V) are obtained, where $R^1$ is lower alkoxy or optionally substituted phenoxy, and $R^2$ is hydrogen, lower alkyl, optionally substituted phenyl or optionally substituted phenylalkyl.

An alterative method for preparing the compounds of formula (VIII) where $R^1$ is lower alkoxy or optionally substituted phenoxy, and $R^2$ is hydrogen, lower alkyl, optionally substituted phenyl or optionally substituted phenylalkyl is depicted in Reaction Sequence III below.

REACTION SEQUENCE III

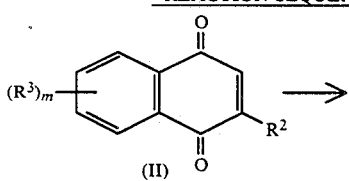

-continued
REACTION SEQUENCE III

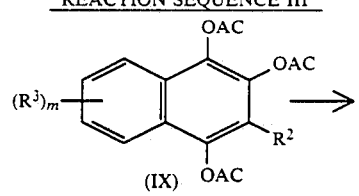

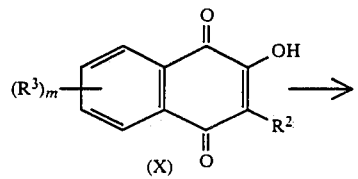

(VIII)

wherein $R^1$, $R^2$, $R^3$ and m are as defined above.

The compound of formula (IX) is prepared by acylating the compound of formula (II) in the presence of a Lewis acid such as boron trifluoride:etherate or a strong inorganic acid, such as perchloric acid, and the like. This reaction is commonly known as the Theile-Winter reaction. The acylating agent is an acid anhydride such as acetic anhydride, propanoic anhydride and the like, preferably acetic anhydride. The compound of formula (IX) wherein $R^2$ is hydrogen may be converted to the compound of formula (IX) wherein $R^2$ is alkyl, optionally substituted phenyl or phenylalkyl by reaction with a peracid anhydride of the formula $(R_2CO_2)_2$ wherein $R^2$ is as defined above and is other than hydrogen. A solution of the unsubstituted compound in a solvent such as glacial acetic acid is heated to 70°–120° C., preferably from 75°–100° C. and an ethereal solution of the anhydride is added dropwise over 1 to 6 hours, preferably over 2 to 4 hours. The compound of formula (IX) wherein $R^2$ is alkyl, optionally substituted phenyl or phenylalkyl is recovered by precipitation. The compound of formula (IX) wherein $R^2$ is hydrogen or alkyl, optionally substituted phenyl or optionally substituted phenylalkyl is then hydrolyzed by treatment with an alkali metal alkoxide in an alcohol, such as sodium methoxide in methanol, followed by treatment with aqueous hydrochloric acid to form the compound of formula (X).

The compound of formula (X) is then converted to the compound of formula (VIII), where $R^1$ is lower alkoxy or optionally substituted phenoxy, and $R^2$ is hydrogen, lower alkyl, optionally substituted phenyl or optionally substituted phenylalkyl, by reaction with an appropriate halide and base.

The compound of formula (X) is reacted with an alkyl halide, e.g. an alkyl bromide or alkyl iodide, or a phenylalkyl halide, in a solvent such as tetrahydrofuran and the like. A solution of 1,5-diazobicyclo[5.4.0]-undec-5-ene (DBU) in a solvent such as tetrahydrofuran is added dropwise. The precipitate of DBU-hydrogen halide which forms is removed by filtration and the compound of formula (VIII) is recovered by evaporation.

The compound of formula (VIII) may also be prepared by reacting the compound of formula (X) with an alcohol such as methanol or ethanol. To a solution of the compound of formula (X) in the appropriate alcohol of formula $R^1H$ is added boron trifluoride:etherate. The solution is heated from 50° to 100° C., preferably from 60° to 80° C. for ½ hour to 4 hours, preferably for 1 to 3 hours. The compound of formula (VIII) is recovered by filtration.

Compounds of Formula I

Compounds of formula (Ia) where X is —C(O)NR$^5$R$^6$ may be prepared by the methods depicted in Reaction Sequences (IVA), (IVB) and (IVC) below.

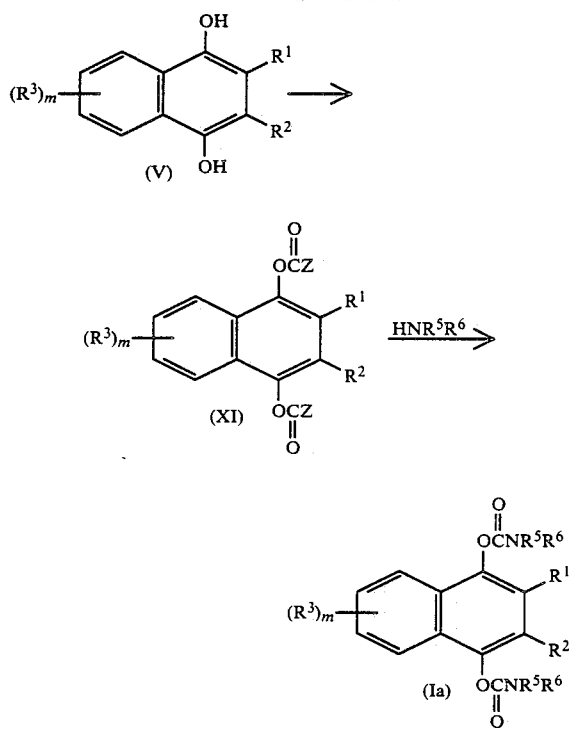

REACTION SEQUENCE IVB

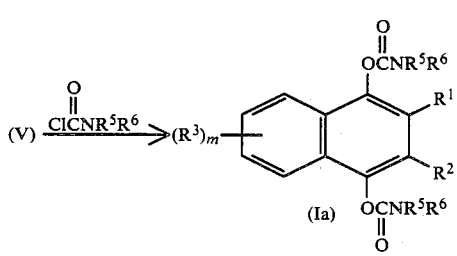

REACTION SEQUENCE IVC

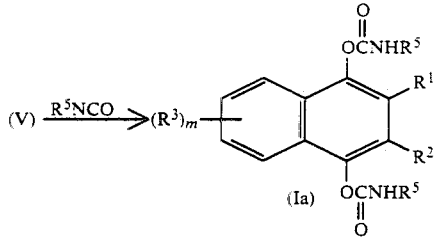

In Reaction Sequence IVA, the preparation starts from the compound of formula (V), prepared as shown in Reaction Sequences I, II and III. To prepare the compound of formula (Ia), where X is —C(O)NR$^5$R$^6$, the compound of formula (V) is first converted to an activated carbonyl derivative of formula (XI), in which Z is a leaving group chosen to be capable of displacement by an amine of formula HNR$^5$R$^6$. For example, Z may be halo, 1-imidazolyl, trichloromethoxy, optionally substituted phenoxy, such as 2,4-dichlorophenoxy, 4-methoxyphenoxy, and the like. For example, the compound of formula (XI) where Z is chloro is made by reaction of a compound of formula (V) with from 1–10 molar equivalents, preferably about 2 molar equivalents, of phosgene in an inert organic solvent such as benzene, acetonitrile, ethyl acetate, tetrahydrofuran, diethyl ether, chloroform, methylene chloride and the like, preferably benzene. The reaction takes place in the presence of from 1–5 molar equivalents, preferably about 2 molar equivalents of a tertiary organic base such as triethylamine or preferably pyridine. The reaction is conducted at from 0°–50° C., preferably about 20°–30° C., for about 1–72 hours, preferably about 16–24 hours, and then filtered. Evaporation of the filtrate under vacuum affords the compound of formula (XI) where Z is chloro.

Alternatively, the compound of formula (V) is reacted as above, substituting an appropriately substituted alkyl or aryl chloroformate for phosgene, giving the compound of formula (XI) where Z is the corresponding substituted alkoxy or aryloxy leaving group Alternatively, the compound of formula (V) is reacted as above, substituting N,N'-carbonyldiimidazole for phosgene, giving the compound of formula (XI) where Z is 1-imidazolyl.

Compounds of formula (Ia) are then prepared by treating the appropriately substituted compound of formula (XI) with an appropriate amine of formula HNR$^5$R$^6$, thereby converting the —OC(O)Z group to the corresponding carbamate. To carry out this process, the compound of formula (XI) is dissolved in an inert solvent as defined above, preferably tetrahydrofuran, and reacted with from about 2–5 molar equivalents, preferably about 2–3 molar equivalents, of the appropriate amine of formula HNR$^5$R$^6$ in solution in an inert solvent as defined above, preferably tetrahydrofuran. The reaction takes place at a temperature of about 0°–40° C., preferably about 20°–30° C., for about 1–10 hours, preferably about 4–6 hours. When the reaction is substantially complete, the product compound of formula (Ia) is isolated by conventional means such as chromatography.

Alternatively, the reaction is carried out in the presence of from 1–5 molar equivalents, preferably 2 molar equivalents, of a tertiary organic base or an inorganic base, as defined above. The compound of formula (XI)

is reacted in the presence of the base with from 1–4 molar equivalents, preferably about 1.2 molar equivalents, of the appropriate amine of formula $HNR^5R^6$ in an inert organic solvent, as defined above.

Alternatively, as shown in Reaction Sequence IVB, compounds of formula (Ia) are made directly from compounds of formula (V), by reaction with an appropriately substituted carbamoyl chloride of formula $ClC(O)NR^5R^6$, where $R^6$ and $R^6$ cannot both be hydrogen. To carry out this process, the compound of formula (V) is dissolved in an inert organic solvent as defined above, preferably tetrahydrofuran, and reacted with from 1–4 molar equivalents, preferably about 1.2 molar equivalents, of the appropriate carbamoyl chloride of formula $ClC(O)NR^5R^6$ in the presence of a tertiary organic base or inorganic base as defined above. The reaction takes place at a temperature of about 0°–40° C., preferably about 20°–30° C., for about 1–10 hours, preferably about 4–6 hours. When the reaction is substantially complete, the product of formula (Ia) is isolated by conventional means such as chromatography.

As shown in Reaction Sequence IVC, compounds of formula (Ia) where $R^6$ is hydrogen can be made by reaction a compound of formula (V) with an appropriately substituted isocyanate of formula $R^5NCO$ where $R^5$ is not hydrogen. To carry out this process, the compound of formula (V) is dissolved in an inert organic solvent as defined above, preferably tetrahydrofuran, and reacted with from 1–5 molar equivalents, preferably about 1.2 molar equivalents, of an isocyanate of formula $R^5NCO$ in the presence of about 0.2 molar equivalents of 4-dimethylaminopyridine. The reaction takes place at a temperature of about 10°–70° C., preferably about 45°–55° C., for about 4–48 hours, preferably about 18–24 hours. When the reaction is substantially complete, the product of formula (Ia) is isolated by conventional means such as chromatography.

Compounds of formula (Ib) where X is $-C(O)OR^4$ may be prepared by the methods depicted in Reaction Sequences (VA) and (VB) below.

REACTION SEQUENCE VA

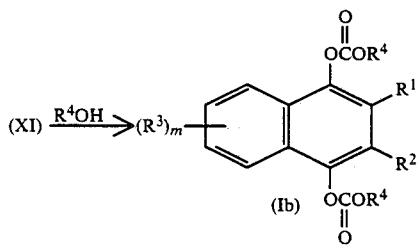

REACTION SEQUENCE VB

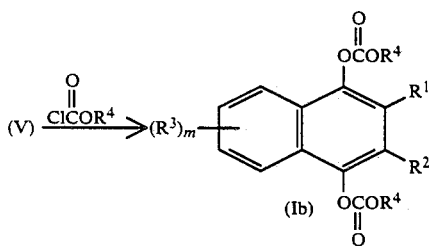

As shown in Reaction Sequence VA, to prepare the compound of formula (Ib), where X is $-C(O)OR^4$, the activated carbonyl derivative of formula (XI), prepared as shown in Reaction Sequence IVA above, is reacted with an alcohol of formula $R^4OH$. To carry out this process the compound of formula (XI) is dissolved in an alcohol of formula $R^4OH$ containing from 1–5 molar equivalents, preferably about 2 molar equivalents of a tertiary organic base such as triethylamine or preferably pyridine. The reaction takes place at a temperature of about 0°–40° C., preferably about 20°–25° C., for about 1–10 hours, preferably about 4–6 hours. When the reaction is substantially complete, the product compound of formula (Ib) is isolated by conventional means.

Alternatively, as shown in Reaction Sequence VB, the compound of formula (V) is reacted as shown above in Reaction Sequence IVA with an appropriate alkyl or aryl chloroformate, or alternatively with an appropriate dialkyl or diaryl dicarbonate, in the presence of a tertiary organic base. For example, the compound of formula (V) is dissolved in an inert solvent as defined above, preferably tetrahydrofuran, and reacted with a chloroformate and a tertiary organic base, preferably triethylamine. The reaction is conducted at a temperature of about 0°–50° C., preferably about 20°–25° C., for about 4–48 hours, preferably about 18–24 hours, giving the compound of formula (Ib), which is isolated by conventional means.

Preparation of Starting Materials

The compounds of formula $HNR^5R^6$ are commercially available from, i.a., Aldrich Chemical Co. Alternatively, they can be prepared by standard methods known to those skilled in the chemical art.

The compounds of formula $ClC(O)NR^5R^6$ are either available commercially from, i.a., Aldrich Chemical Co. or they can be prepared by, for example, reaction of a secondary amine of formula $HNR^5R^6$ with phosgene. Compounds of formula $ClC(O)NR^5R^6$ wherein $R^5$ is hydrogen can be prepared by the reaction of an isocyanate of formula $R^6NCO$, where $R^6$ is not hydrogen, with an excess of dry hydrochloric acid in an inert solvent. These reactions are described in greater detail in *Comprehensive Organic Chemistry*, Vol. 2, by Barton and Ollis, pp. 1088–1090.

Any alkyl or aryl chloroformates that are not commercially available are prepared, for example, by reaction of phosgene with one equivalent of the appropriate alcohol or phenol in the presence of a base. The reactions are described in greater detail in *Comprehensive Organic Chemistry*, by Barton and Ollis, Vol 2, pp 1078–1083 and Vol 3, pp 432–4.

The compounds of formula $R^6NCO$, where $R^6$ is not hydrogen, that are not commercially available are prepared by reaction of an appropriately substituted primary amine ($R^6NH_2$) with phosgene. The reaction is discussed in further detail in *Organic Functional Group Preparations*, 2nd Edition, Vol. 1, by Sandler and Karo, pp. 364–365.

In summary, the compounds of the present invention are made by the procedures below:

1. The process for preparing compounds of formula (Ia) wherein:

$R^1$ is lower alkoxy of one to six carbon atoms or phenoxy optionally substituted by one or two substituents chosen from lower alkyl of one to four carbon atoms, lower alkoxy of one to four carbon atoms and halo;

$R^2$ is the same as $R^1$, or $R^2$ is hydrogen, lower alkyl of one to six carbon atoms, phenyl or phenyl-lower-alkyl, wherein the phenyl ring of the phenyl or phenyl-lower-alkyl group is optionally substituted by one or two substituents chosen from lower alkyl of one to four carbon atoms, lower alkoxy of one to four carbon atoms and halo;

$R^3$ is hydrogen, halo, lower alkyl of one to six carbon atoms, lower alkoxy of one to six carbon atoms, phenyl, phenyl-lower-alkyl or phenyl-lower-alkoxy, wherein the phenyl ring of the phenyl, phenyl-lower-alkyl or phenyl-lower-alkoxy group is optionally substituted by one or two substituents chosen from lower alkyl of one to four carbon atoms, lower alkoxy of one to four carbon atoms and halo;

m is 1 or 2; and

X is the same and is $-C(O)NR^5R^6$, wherein $R^5$ and $R^6$ are independently hydrogen, lower alkyl of one to six carbon atoms, cycloalkyl of five to eight carbon atoms or phenyl optionally substituted with one or two substitutents chosen from lower alkyl of one to four carbon atoms, lower alkoxy of one to four carbon atoms and halo;

which comprises:

(a) reacting a compound of the formula

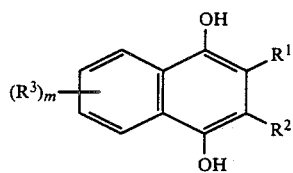

(V)

wherein $R^1$, $R^2$, $R^3$ and m are as defined above, with an isocyanate of the formula $R^6NCO$, where $R^6$ is as defined above but is not hydrogen, or (b) reacting a compound of the formula (V) with a carbamoyl chloride of the formula $ClC(O)NR^5R^6$, where $R^5$ and $R^6$ are as defined above but $R^6$ is not hydrogen.

2. Alternatively, the process for the preparation of the compounds of the formula (Ia), which comprises:

reacting a compound of the formula

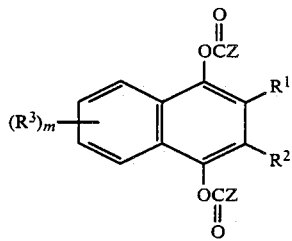

(XI)

wherein $R^1$, $R^2$, $R^3$ and m are as defined above, and $-C(O)Z$ is an activated carbonyl complex where X is as defined supra, with an appropriate amine of the formula $HNR^5R^6$, where $R^5$ and $R^6$ are as defined above.

3. The process for the preparation of the compounds of the formula (Ib), wherein $R^1$, $R^2$, $R^3$ and m are as defined above, and X is the same and is $-C(O)R^4$, where $R^4$ is alkyl of one to seven carbon atoms, phenyl or benzyl, wherein the phenyl ring of the phenyl or benzyl group is optionally substituted by one or two substituents chosen from lower alkyl of one to four carbon atoms, lower alkoxy of one to four carbon atoms and halo;

which comprises:

reacting a compound of the formula

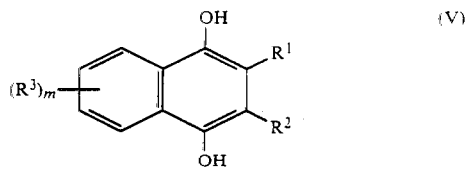

(V)

wherein $R^1$, $R^2$, $R^3$ and m are as defined above, with (a) a chloroformate of the formula $ClC(O)OR^4$, where $R^4$ is as defined above, or (b) a dicarbonate of the formula $R^4OC(O)OC(O)OR^4$, where $R^4$ is as defined above.

4. Alternatively, the process for the preparation of the compounds of the formula (Ib), which comprises:

reacting a compound of the formula

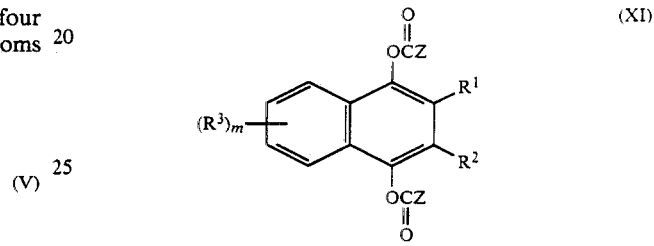

(XI)

wherein $R^1$, $R^2$, $R^3$ and m are as defined above, and $-C(O)Z$ is an activated carbonyl complex where Z is as defined supra, with an appropriate alcohol of the formula $R^4OH$, where $R^4$ is as defined above.

The following specific description is given to enable those skilled in the art to more clearly understand and practice the present invention. It should not be considered as a limitation upon the scope of the invention but merely as illustrative and representative thereof.

PREPARATION 1

(Preparation of 2,3-dimethoxy-1,4-naphthoquinone and related compounds of formula (IV)

To a mechanically stirred solution of sodium methoxide (11.1 g) in anhydrous methanol (200 mL) under a blanket of nitrogen was added 2,3-dichloro-1,4-naphthoquinone (22.7 g) as rapidly as possible. The temperature rose to 50° C. during the addition, and the reaction was then heated to reflux for 1 hour. The mixture was cooled and acidified with 6M hydrochloric acid to give a brilliant yellow color. After the addition of water (800 mL), the reaction mixture was filtered, and the precipitate was washed with aqueous methanol (4:1 water-methanol) until the filtrate was yellow-orange. The precipitate was air dried to yield 21.2 g of 2,3-dimethoxy-1,4-naphthoquinone, m.p. 116°-117° C.

Similarly, optionally substituting the appropriate sodium alkoxide for sodium methoxide and optionally substituting the appropriate compound of formula (III) for 2,3-dichloro-1,4-naphthoquinone, the following compounds are prepared:

2,3-diethoxy-1,4-naphthoquinone;
2,3-di-n-propoxy-1,4-naphthoquinone;
6-chloro-2,3-dimthoxy-1,4-naphthoquinone;
6,7-dimethyl-2,3-dimethoxy-1,4-naphthoquinone;
6-bromo-2,3-dimethoxy-1,4-naphthoquinone;
6-fluoro-2,3-dimethoxy-1,4-naphthoquinone;
6-chloro-2,3-diethoxy-1,4-naphthoquinone;
6-methyl-2,3-dimethoxy-1,4-naphthoquinone;

6-i-propyl-2,3-dimethoxy-1,4-naphthoquinone;
6-phenyl-2,3-dimethoxy-1,4-naphthoquinone;
6-benzyl-2,3-dimethoxy-1,4-naphthoquinone;
2,3-di-n-butoxy-6-chloro-1,4-naphthoquinone;
6-chloro-2,3-di-i-butoxy-1,4-naphthoquinone;
6-chloro-2,3-(2,2-dimethylpropoxy)-1,4-naphthoquinone;
2,3-di-s-butoxy-1,4-naphthoquinone;
2,3-di(2,2-dimethylpropoxy)-1,4-naphthoquinone;
2,3-di-n-hexyloxy-1,4-naphthoquinone;
2,3-di-n-butoxy-1,4-naphthoquinone;
2,3-diphenoxy-1,4-naphthoquinone;
6-chloro-2,3-diphenoxy-1,4-naphthoquinone;
6-chloro-2,3-di(4-ethylphenoxy)-1,4-naphthoquinone;
6-chloro-2,3-di(2-fluorophenoxy)-1,4-naphthoquinone;
6-chloro-2,3-di(4-t-butylphenoxy)-1,4-naphthoquinone;
6-chloro-2,3-di(2,6-dimethylphenoxy)-1,4-naphthoquinone; and
6-chloro-2,3-di(2-ethoxyphenoxy)-1,4-naphthoquinone.

PREPARATION 2

Preparation of 2-ethyl-1,4-naphthoquinone and related compounds of formula (II)

A solution of 1,4-naphthoquinone (7.91 g), propanoic acid (3.70 g) and silver nitrate (1.53 g) in a mixture of acetonitrile (11.4 mL), sulfolane (34.1 mL) and water (79.5 mL) was heated at 60°–65° C. for 2 hours. A solution of ammonium persulfate (13.7 g) in water (25 mL) was then added dropwise. The mixture was cooled in ice water and extracted with ether. The organic layer was washed with saturated sodium bicarbonate, water and brine, then dried, filtered and evaporated. Chromatography over silica gel afforded 2-ethyl-1,4-naphthoquinone, m.p. 87°–88° C.

Similarly, using the above procedure but optionally replacing 1,4-naphthoquinone with an appropriately substituted 1,4-naphthoquinone, or optionally replacing propanoic acid with an appropriate carboxylic acid, the following compounds may be prepared:
2-methyl-1,4-naphthoquinone;
2-n-propyl-1,4-naphthoquinone;
2,6-dimethyl-1,4-naphthoquinone;
2-ethyl-5-methyl-1,4-naphthoquinone;
2-sec-butyl-1,4-naphthoquinone;
2-n-pentyl-1,4-naphthoquinone;
2-ethyl-5-fluoro-1,4-naphthoquinone;
3-ethyl-6-methoxy-1,4-naphthoquinone;
2-methyl-6-benzyloxy-1,4-naphthoquinone;
2-ethyl-6-methoxy-1,4-naphthoquinone;
2-methyl-6-fluoro-1,4-naphthoquinone;
2-isopropyl-1,4-naphthoquinone;
2-n-hexyl-1,4-naphthoquinone;
2-methyl-6-chloro-1,4-naphthoquinone;
2,5-dimethyl-1,4-naphthoquinone;
2-methyl-6-phenyl-1,4-naphthoquinone;
2-methyl-5-methoxy-1,4-naphthoquinone;
2-methyl-5-ethoxy-1,4-naphthoquinone;
2-methyl-6-benzyloxy-1,4-naphthoquinone;
2-ethyl-5-chloro-1,4-naphthoquinone;
2-isopropyl-5-phenyl-1,4-naphthoquinone;
2-n-hexyl-6-methyl-1,4-naphthoquinone;
2-n-propyl-6-chloro-1,4-naphthoquinone;
2-n-propyl-6-fluoro-1,4-naphthoquinone;
2-phenyl-1,4-naphthoquinone;
2,6,7-trimethyl-1,4-naphthoquinone;
2-t-butyl-1,4-naphthoquinone; and
2-n-propyl-6-methyl-1,4-naphthoquinone.

PREPARATION 3A

Preparation of compounds of formula (VII)

A. Chlorine was bubbled through a solution of 1,4-naphthoquinone (39.5 g) in glacial acetic acid maintained at 15° C. by cooling. The precipitated intermediate dichloride was isolated by filtration and then suspended in fresh glacial acetic acid (500 mL). Anhydrous sodium acetate (25 g) was added, and the mixture was brought to reflux. Water was then added, and the mixture was allowed to cool, precipitating 2-chloro-1,4-naphthoquinone, collected by filtration and air drying, m.p. 118° C.

B. 2-Chloro-3-methyl-1,4-naphthoquinone was prepared analogously, except that the intermediate dichloride was isolated as an oil after evaporation, aqueous extraction with ether and evaporation. Conversion of this intermediate using sodium acetate in acetic acid gave 2-chloro-3-methyl-1,4-naphthoquinone, m.p. 155°–156° C.

C. Similarly, using the procedure in paragraph A above, but optionally replacing 1,4-naphthoquinone with an appropriately substituted 1,4-naphthoquinone, the following compounds may be prepared:
2-chloro-3,8-dimethyl-1,4-naphthoquinone;
2-chloro-3-methyl-8-methoxy-1,4-naphthoquinone;
2-chloro-3-methyl-7-benzyloxy-1,4-naphthoquinone;
2-chloro-3-ethyl-8-chloro-1,4-naphthoquinone;
2-chloro-3-isopropyl-8-phenyl-1,4-naphthoquinone;
2-chloro-3-n-hexyl-7-methyl-1,4-naphthoquinone;
2-chloro-3-n-propyl-7-chloro-1,4-naphthoquinone;
2-chloro-3-n-propyl-7-fluoro-1,4-naphthoquinone;
2,6-dichloro-1,4-naphthoquinone;
2,5-dichloro-1,4-naphthoquinone;
2-chloro-6-methoxy-1,4-naphthoquinone;
2-chloro-6-ethoxy-1,4-naphthoquinone;
2-chloro-6-methyl-1,4-naphthoquinone;
2-chloro-6-ethyl-1,4-naphthoquinone;
2-chloro-3-ethyl-1,4-naphthoquinone;
2-chloro-3-n-propyl-1,4-naphthoquinone;
2-chloro-3,7-dimethyl-1,4-naphthoquinone;
2-chloro-3-ethyl-8-methyl-1,4-naphthoquinone;
2-chloro-3-phenyl-1,4-naphthoquinone;
2-chloro-3-isopropyl-1,4-naphthoquinone;
2-chloro-3-sec-butyl-1,4-naphthoquinone;
2-chloro-3-n-pentyl-1,4-naphthoquinone;
2-chloro-3-n-hexyl-1,4-naphthoquinone;
2-chloro-3-ethyl-8-fluoro-1,4-naphthoquinone;
2-chloro-3-methyl-7-phenyl-1,4-naphthoquinone;
2-chloro-6-bromo-1,4-naphthoquinone;
2-chloro-6-fluoro-1,4-naphthoquinone;
2-chloro-6-methyl-1,4-naphthoquinone;
2-chloro-6-i-propyl-1,4-naphthoquinone;
2-chloro-6-phenyl-1,4-naphthoquinone;
2-chloro-6-benzyl-1,4-naphthoquinone;
2-chloro-6,7-dimethyl-1,4-naphthoquinone;
2-chloro-5-methoxy-1,4-naphthoquinone;
2-chloro-5-phenyl-1,4-naphthoquinone;
2,7-dichloro-1,4-naphthoquinone;
2-chloro-7-methyl-1,4-naphthoquinone;
2-chloro-3-ethyl-1,4-naphthoquinone;
2-chloro-3-methyl-1,4naphthoquinone;
2-chloro-3-ethyl-7-methoxy-1,4-naphthoquinone;
2-chloro-3-methyl-6-ethoxy-1,4-naphthoquinone;
2-chloro-3-methyl-7-benzyloxy-1,4-naphthoquinone;
2,6-dichloro-3-methyl-1,4-naphthoquinone;
2-chloro-3,6,7-trimethyl-1,4-naphthoquinone;

2-chloro-3n-propyl-7-methyl-1,4-naphthoquinone;
2-chloro-3-t-butyl-1,4-naphthoquinone; and
2,6-dichloro-3-n-propyl-1,4-naphthoquinone.

PREPARATION 3B

Preparation of compounds of formula (III)

A. Chlorine was bubbled through a solution of 1,4-naphthoquinone (16.0 g) and iodine (1.20 g) in glacial acetic acid while refluxing the mixture for 2 hours. Water was then added, and the mixture was allowed to cool, precipitating 2,3-dichloro-1,4-naphthoquinone, collected by filtration and air drying, m.p. 147°–148° C.

B. Similarly, using the procedure in paragraph A above, but optionally replacing 1,4-naphthoquinone with an appropriately substituted 1,4-naphthoquinone, the following compounds may be prepared:
2,3,6-trichloro-1,4-naphthoquinone;
2,3-dichloro-6-fluoro-1,4-naphthoquinone;
2,3-dichloro-6-methoxy-1,4-naphthoquinone;
2,3-dichloro-6-methyl-1,4-naphthoquinone;
2,3-dichloro-6,7-dimethyl-1,4-naphthoquinone; and
2,3-dichloro-6-phenyl-1,4-naphthoquinone.

PREPARATION 4

Preparation of compounds of formula (VIII)

A. A solution of 2-chloro-1,4-naphthoquinone (10.3 g) in tetrahydrofuran (100 mL) was treated with a suspension of sodium methoxide (3.20 g) in tetrahydrofuran (25 mL) at room temperature. After stirring overnight, the mixture was evaporated, and the residue was taken up in ether. The organic layer was washed with brine, dried, filtered and evaporated. Chromatography over silica gel gave 2-methoxy-1,4-naphthoquinone, m.p. 182°–183° C.

B. Similarly, replacing the 2-chloro-1,4-naphthoquinone with other compounds of formula (VII) and following the above procedure, the following compounds were prepared:
2-ethoxy-1,4-naphthoquinone, m.p. 122°–123° C.;
2-methoxy-3-methyl-1,4-naphthoquinone, m.p. 93°–94° C.;
2-n-propoxy-1,4-naphthoquinone, m.p. 93°–94° C.;
2-isopropoxy-3-methyl-1,4-naphthoquinone, m.p. 114°–115° C.;
2-n-butoxy-1,4-naphthoquinone, m.p. 110°–111° C.;
2-ethoxy-3-methyl-1,4-naphthoquinone, m.p. 67°–68° C.;
2-n-propoxy-3-methyl-1,4-naphthoquinone, oil; and
2-isopropoxy-3-methyl-1,4-naphthoquinone, oil.

C. Similarly, replacing the 2-chloro-1,4-naphthoquinone with other compounds of formula (VII) and following the above procedure, the following compounds are prepared:
2-methoxy-3,8-dimethyl-1,4-naphthoquinone;
2,8-dimethoxy-3-methyl-1,4-naphthoquinone;
2-methoxy-3-methyl-7-benzyloxy-1,4-naphthoquinone;
2-methoxy-3-ethyl-8-chloro-1,4-naphthoquinone;
2-methoxy-3-isopropyl-8-phenyl-1,4-naphthoquinone;
2-methoxy-3-n-hexyl-7-methyl-1,4-naphthoquinone;
2-methoxy-3-n-propyl-7-chloro-1,4-naphthoquinone;
2-methoxy-3-n-propyl-7-fluoro-1,4-naphthoquinone;
2-methoxy-6-chloro-1,4-naphthoquinone;
2-methoxy-5-chloro-1,4-naphthoquinone;
2,6-dimethoxy-1,4-naphthoquinone;
2-methoxy-6-ethoxy-1,4-naphthoquinone;
2-methoxy-6-methyl-1,4-naphthoquinone; 2-methoxy-6-ethyl-1,4-naphthoquinone;
2-methoxy-3-ethyl-1,4-naphthoquinone;
2-methoxy-3-n-propyl-1,4-naphthoquinone;
2-methoxy-3,7-dimethyl-1,4-naphthoquinone;
2-methoxy-3-ethyl-8-methyl-1,4-naphthoquinone;
2-methoxy-3-phenyl-1,4-naphthoquinone;
2-methoxy-3-isopropyl-1,4-naphthoquinone;
2-methoxy-3-sec-butyl-1,4-naphthoquinone;
2-methoxy-3-n-pentyl-1,4-naphthoquinone;
2-methoxy-3-n-hexyl-1,4-naphthoquinone;
2-methoxy-3-ethyl-8-fluoro-1,4-naphthoquinone;
2-methoxy-3-methyl-7-phenyl-1,4-naphthoquinone;
2-methoxy-6-bromo-1,4-naphthoquinone;
2-methoxy-6-fluoro-1,4-naphthoquinone;
2-methoxy-6-methyl-1,4-naphthoquinone;
2-methoxy-6-i-propyl-1,4-naphthoquinone;
2-methoxy-6-phenyl-1,4-naphthoquinone;
2-methoxy-6-benzyl-1,4-naphthoquinone;
2-methoxy-6,7-dimethyl-1,4-naphthoquinone;
2,5-dimethoxy-1,4-naphthoquinone;
2-methoxy-5-phenyl-1,4-naphthoquinone;
2-methoxy-7-chloro-1,4-naphthoquinone;
2-methoxy-7-methyl-1,4-naphthoquinone;
2-methoxy-3-ethyl-1,4-naphthoquinone;
2-methoxy-3-t-butyl-1,4-naphthoquinone;
2,7-dimethoxy-3-ethyl-1,4-naphthoquinone;
2-methoxy-3-methyl-6-ethoxy-1,4-naphthoquinone;
2-methoxy-3-methyl-7-benzyloxy-1,4-naphthoquinone;
2-methoxy-6-chloro-3-methyl-1,4-naphthoquinone;
2-methoxy-3,6,7-trimethyl-1,4-naphthoquinone;
2-methoxy-3-n-propyl-7-methyl-1,4-naphthoquinone;
2-methoxy-6-chloro-3-n-propyl-1,4-naphthoquinone;
2-ethoxy-3-ethyl-1,4-naphthoquinone;
2-ethoxy-3-n-propyl-1,4-naphthoquinone;
2-ethoxy-3-isobutyl-1,4-naphthoquinone;
2-ethoxy-6-bromo-1,4-naphthoquinone;
2-ethoxy-6-fluoro-1,4-naphthoquinone;
2-ethoxy-6-methyl-1,4-naphthoquinone;
2-ethoxy-6-i-propyl-1,4-naphthoquinone;
2-ethoxy-6-phenyl-1,4-naphthoquinone;
2-ethoxy-6-benzyl-1,4-naphthoquinone;
2-ethoxy-6,7-dimethyl-1,4-naphthoquinone;
2-ethoxy-5-methoxy-1,4-naphthoquinone;
2-ethoxy-5-phenyl-1,4-naphthoquinone;
2-ethoxy-6-chloro-1,4-naphthoquinone;
2-ethoxy-7-methyl-1,4-naphthoquinone;
2-ethoxy-3-ethyl-5-fluoro-1,4-naphthoquinone;
2-ethoxy-3-methyl-5-phenyl-1,4-naphthoquinone;
2-n-propoxy-3-ethyl-1,4-naphthoquinone;
2-n-propoxy-3-n-propyl-1,4-naphthoquinone;
2-n-propoxy-3-n-hexyl-1,4-naphthoquinone;
2-isopropoxy-3-ethyl-1,4-naphthoquinone;
2-isopropoxy-3-n-propyl-1,4-naphthoquinone;
2-isopropoxy-3-n-hexyl-1,4-naphthoquinone;
2-n-butoxy-3-methyl-1,4-naphthoquinone;
2-n-butoxy-3-ethyl-1,4-naphthoquinone;
2-s-butoxy-1,4-naphthoquinone;
2-n-pentyloxy-1,4-naphthoquinone;
2-n-pentyloxy-3-methyl-1,4-naphthoquinone;
2-s-pentyloxy-1,4-naphthoquinone;
2-n-hexyloxy-1,4-naphthoquinone;
2-n-hexyloxy-3-methyl-1,4-naphthoquinone;
2(2,2-dimethylpropoxy)-1,4-naphthoquinone;
2-phenoxy-1,4-naphthoquinone;
2-(4-chlorophenoxy)-1,4-naphthoquinone;
2-(4-methoxyphenoxy)-1,4-naphthoquinone;
2-(2,4-dichlorophenoxy)-1,4-naphthoquinone;
2-t-butyloxy-1,4-naphthoquinone; and
2-(3-metylphenoxy)-1,4-naphthoquinone.

PREPARATION 5

(Preparation of 2-methoxy-1,4-dihydroxynaphthalene and related compounds of formula (V))

A. A solution of 2-methoxy-1,4-naphthoquinone (20.0 g) in tetrahydrofuran (150 mL) was hydrogenated at atmospheric pressure over Pd-C (10%, 0.5 g) until the calculated amount of hydrogen was absorbed, approximately 4 hours. Filtering off the catalyst under an atmosphere of nitrogen gave a solution of the desired product, which was used as such without isolation of the product as the starting material in Examples 1, 2 and 3, infra. Alternatively, the solvent is removed under reduced pressure and the residue recrystallized from diethyl ether/pentane, affording 2-methoxy-1,4-dihydroxynaphthalene.

B. Similarly, proceeding as above, substituting the appropriate compound of formula (IV) or (VIII) for 2-methoxy-1,4-naphthoquinone, the following compounds, for example, were prepared:
2,3-dimethoxy-1,4-dihydroxynaphthalene.
2,3-dimethoxy-1,4-dihydroxy-6-chloronaphthalene.
2,3-diphenoxy-1,4-dihydroxynaphthalene.
2,3-diphenoxy-1,4-dihydroxy-6-chloronaphthalene.
2-methoxy-3-methyl-1,4-dihydroxynaphthalene.

C. Similarly proceeding as above, substituting the appropriate compound of formula (IV) or (VIII) for 2-methoxy-1,4-naphthoquinone, the following compounds of formula (V), for example, are prepared:
2-methoxy-3,8-dimethyl-1,4-dihydroxynaphthalene;
2,8-dimethoxy-3-methyl-1,4-dihydroxynaphthalene;
2-methoxy-3-methyl-7-benzyloxy-1,4-dihydroxynaphthalene;
2-methoxy-3-ethyl-8-chloro-1,4-dihydroxynaphthalene;
2-methoxy-3-isopropyl-8-phenyl-1,4-dihydroxynaphthalene;
2-methoxy-3-t-butyl-1,4-dihydroxynaphthalene;
2-methoxy-3-n-hexyl-7-methyl-1,4-dihydroxynaphthalene;
2-methoxy-3-n-propyl-7-chloro-1,4-dihydroxynaphthalene;
2-methoxy-3-n-propyl-7-fluoro-1,4-dihydroxynaphthalene;
2-methoxy-6-chloro-1,4-dihydroxynaphthalene;
2-methoxy-5-chloro-1,4-dihydroxynaphthalene;
2,6-dimethoxy-1,4-dihydroxynaphthalene;
2-methoxy-6-ethoxy-1,4-dihydroxynaphthalene;
2-methoxy-6-methyl-1,4-dihydroxynaphthalene;
2-methoxy-6-ethyl-1,4-dihydroxynaphthalene;
2-methoxy-3-ethyl-1,4-dihydroxynaphthalene;
2-methoxy-3-n-propyl-1,4-dihydroxynaphthalene;
2-methoxy-3,7-dimethyl-1,4-dihydroxynaphthalene;
2-methoxy-3-ethyl-8-methyl-1,4-dihydroxynaphthalene;
2-methoxy-3-phenyl-1,4-dihydroxynaphthalene;
2-methoxy-3-isopropyl-1,4-dihydroxynaphthalene;
2-methoxy-3-sec-butyl-1,4-dihydroxynaphthalene;
2-methoxy-3-n-pentyl-1,4-dihydroxynaphthalene;
2-methoxy-3-n-hexyl-1,4-dihydroxynaphthalene;
2-methoxy-3-ethyl-8-fluoro-1,4-dihydroxynaphthalene;
2-methoxy-3-methyl-7-phenyl-1,4-dihydroxynaphthalene;
2-methoxy-6-bromo-1,4-dihydroxynaphthalene;
2-methoxy-6-fluoro-1,4-dihydroxynaphthalene;
2-methoxy-6-methyl-1,4-dihydroxynaphthalene;
2-methoxy-6-i-propyl-1,4-dihydroxynaphthalene;
2-methoxy-6-phenyl-1,4-dihydroxynaphthalene;
2-methoxy-6-benzyl-1,4-dihydroxynaphthalene;
2-methoxy-6,7-dimethyl-1,4-dihydroxynaphthalene;
2,5-dimethoxy-1,4-dihydroxynaphthalene;
2-methoxy-5-phenyl-1,4-dihydroxynaphthalene;
2-methoxy-7-chloro-1,4-dihydroxynaphthalene;
2-methoxy-7-methyl-1,4-dihydroxynaphthalene;
2-methoxy-7-ethyl-1,4-dihydroxynaphthalene;
2-methoxy-3-methyl-1,4-dihydroxynaphthalene;
2,7-dimethoxy-3-ethyl-1,4-dihydroxynaphthalene;
2-methoxy-3-methyl-6-ethoxy-1,4-dihydroxynaphthalene;
2-methoxy-3-methyl-7-benzyloxy-1,4-dihydroxynaphthalene;
2-methoxy-6-chloro-3-methyl-1,4-dihydroxynaphthalene;
2-methoxy-3,6,7-trimethyl-1,4-dihydroxynaphthalene;
2-methoxy-3-n-propyl-7-methyl-1,4-dihydroxynaphthalene;
2-methoxy-6-chloro-3-n-propyl-1,4-dihydroxynaphthalene;
2-ethoxy-1,4-dihydroxynaphthalene;
2-ethoxy-3-methyl-1,4-dihydroxynaphthalene;
2-ethoxy-3-ethyl-1,4-dihydroxynaphthalene;
2-ethoxy-3-n-propyl-1,4-dihydroxynaphthalene;
2-ethoxy-3-isobutyl-1,4-dihydroxynaphthalene;
2-ethoxy-6-bromo-1,4-dihydroxynaphthalene;
2-ethoxy-6-fluoro-1,4-dihydroxynaphthalene;
2-ethoxy-6-methyl-1,4-dihydroxynaphthalene;
2-ethoxy-6-i-propyl-1,4-dihydroxynaphthalene;
2-ethoxy-6-phenyl-1,4-dihydroxynaphthalene;
2-ethoxy-6-benzyl-1,4-dihydroxynaphthalene;
2-ethoxy-6,7-dimethyl-1,4-dihydroxynaphthalene;
2-ethoxy-5-methoxy-1,4-dihydroxynaphthalene;
2-ethoxy-5-phenyl-1,4-dihydroxynaphthalene;
2-ethoxy-6-chloro-1,4-dihydroxynaphthalene;
2-ethoxy-7-methyl-1,4-dihydroxynaphthalene;
2-ethoxy-3-ethyl-5-fluoro-1,4-dihydroxynaphthalene;
2-ethoxy-3-methyl-5-phenyl-1,4-dihydroxynaphthalene;
2-n-propoxy-1,4-dihydroxynaphthalene;
2-n-propoxy-3-methyl-1,4-dihydroxynaphthalene;
2-n-propoxy-3-ethyl-1,4-dihydroxynaphthalene;
2-n-propoxy-3-n-propyl-1,4-dihydroxynaphthalene;
2-n-butoxy-1,4-dihydroxynaphthalene;
2-n-butoxy-3-methyl-1,4-dihydroxynaphthalene;
2-t-butoxy-1,4-dihydroxynaphthalene;
2-n-butoxy-3-ethyl-1,4-dihydroxynaphthalene;
2-s-butoxy-1,4-dihydroxynaphthalene;
2-n-pentyloxy-1,4-dihydroxynaphthalene;
2-n-pentyloxy-3-methyl-1,4-dihydroxynaphthalene;
2-s-pentyloxy-1,4-dihydroxynaphthalene;
2-n-hexyloxy-1,4-dihydroxynaphthalene;
2-n-hexyloxy-3-methyl-1,4-dihydroxynaphthalene;
2(2,2-dimethylpropoxy)-1,4-dihydroxynaphthalene;
2-phenoxy-1,4-dihydroxynaphthalene;
2-(4-chlorophenoxy)-1,4-dihydroxynaphthalene;
2-(4-methoxyphenoxy)-1,4-dihydroxynaphthalene;
2-(2,4-dichlorophenoxy)-1,4-dihydroxynaphthalene;
2-(3-methylphenoxy)-1,4-dihydroxynaphthalene;
2,3-dimethoxy-1,4-dihydroxy-6-chloronaphthalene;
2,3-dimethoxy-1,4-dihydroxy-6-bromonaphthalene;
2,3-dimethoxy-1,4-dihydroxy-6-fluoronaphthalene;
2,3-dimethoxy-1,4-dihydroxy-6-ethoxynaphthalene;
2,3-dimethoxy-1,4-dihydroxy-6-phenylnaphthalene;
2,3-dimethoxy-1,4-dihydroxy-6,7-dimethylnaphthalene;
2,3-diethoxy-1,4-dihydroxynaphthalene;
2,3-diethoxy-1,4-dihydroxy-6-chloronaphthalene;
2,3-diethoxy-1,4-dihydroxy-6-methoxynaphthalene;
2,3-di-n-propoxy-1,4-dihydroxynaphthalene;

2,3-diisopropoxy-1,4-dihydroxynaphthalene;
2,3-di-n-butoxy-1,4-dihydroxynaphthalene;
2,3-di-n-hexyloxy-1,4-dihydroxynaphthalene;
2,3-di(2-methylhexyloxy)-1,4-dihydroxynaphthalene;
2,3-di(4-chlorophenoxy)-1,4-dihydroxynaphthalene;
2,3-di(4-methoxyphenoxy)-1,4-dihydroxynaphthalene;
2,3-di(2,4-dichlorophenoxy)-1,4-dihydroxynaphthalene; and
2,3-di(3-methylphenoxy)-1,4-dihydroxynaphthalene.

EXAMPLE 1

Preparation of 2,3-dimethoxy-1,4-di(methylcarbamoyloxy)naphthalene and related compounds of formula (Ia) where $R^6$ is hydrogen A. To a solution of 1.00 g of 2,3-dimethoxy-1,4-dihydroxynaphthalene, prepared as shown in Preparation 5, in 50 ml of tetrahydrofuran was added 0.670 g of methyl isocyanate followed by 0.12 g of 4-dimethylaminopyridine. The solution was stirred at room temperature overnight. The solvent was removed under reduced pressure and the residue dissolved in ethyl acetate, washed with dilute hydrochloric acid and dried over anhydrous sodium sulfate. The solvent was removed under reduced pressure and the residue chromatographed on silica gel, eluting with methylene chloride, giving 2,3-dimethoxy-1,4-di(methylcarbamoyloxy)naphthalene, m.p. 228°–229° C.

B. Similarly, starting with the appropriate compound of formula (V) and the appropriate isocyanate, the following compounds of formula (Ia) were prepared:
2,3-dimethoxy-1,4-di(ethylcarbamoyloxy)naphthalene, m.p. 198°–199° C.
2,3-dimethoxy-1,4-di(methylcarbamoyloxy)-6-chloronaphthalene, m.p. 185°–187° C.
2,3-dimethoxy-1,4-di(ethylcarbamoyloxy)-6-chloronaphthalene, m.p. 197°–198° C.
2,3-diphenoxy-1,4-di(methylcarbamoyloxy)naphthalene, m.p. 245°–246° C.
2,3-diphenoxy-1,4-di(methylcarbamoyloxy)-6-chloronaphthalene, m.p. 226°–227° C.
2-methoxy-1,4-di(methylcarbamoyloxy)naphthalene, m.p. 199°–200° C.
2-methoxy-3-methyl-1,4-di(methylcarbamoyloxy)naphthalene, m.p. 255°–256° C.

C. Similarly, starting with the appropriate compound of formula (V) and the appropriate isocyanate, the following exemplary compounds of formula (Ia) are prepared:
2,3-dimethoxy-1,4-di(methylcarbamoyloxy)-6-bromonaphthalene;
2,3-dimethoxy-1,4-di(ethylcarbamoyloxy)-6-fluoronaphthalene;
2,3-dimethoxy-1,4-di(methylcarbamoyloxy)-6,7-dimethylnaphthalene;
2,3-dimethoxy-1,4-di(methylcarbamoyloxy)-6-phenylnaphthalene;
2,3-dimethoxy-1,4-di(n-propylcarbamoyloxy)naphthalene;
2,3-dimethoxy-1,4-di(isopropylcarbamoyloxy)naphthalene;
2,3-dimethoxy-1,4-di(n-butylcarbamoyloxy)naphthalene;
2,3-dimethoxy-1,4-di(n-hexylcarbamoyloxy)naphthalene;
2,3-dimethoxy-1,4-di(2-methylhexylcarbamoyloxy)naphthalene;
2,3-dimethoxy-1,4-di(cyclohexylcarbamoyloxy)naphthalene;
2,3-dimethoxy-1,4-di(phenylcarbamoyloxy)naphthalene;
2,3-dimethoxy-1,4-di(benzylcarbamoyloxy)naphthalene;
2,3-dimethoxy-1,4-di(methylcarbamoyloxy)-6-chloronaphthalene;
2,3-diethoxy-1,4-di(ethylcarbamoyloxy)-6-fluoronaphthalene;
2,3-diethoxy-1,4-di(methylcarbamoyloxy)-6,7-dimethylnaphthalene;
2,3-diethoxy-1,4-di(ethylcarbamoyloxy)-6-phenylnaphthalene;
2,3-diethoxy-1,4-di(n-propylcarbamoyloxy)naphthalene;
2,3-diethoxy-1,4-di(isopropylcarbamoyloxy)naphthalene;
2,3-diethoxy-1,4-di(n-butylcarbamoyloxy)naphthalene;
2,3-diethoxy-1,4-di(n-hexylcarbamoyloxy)naphthalene;
2,3-diethoxy-1,4-di(2-methylhexylcarbamoyloxy)naphthalene;
2,3-diethoxy-1,4-di(cyclohexylcarbamoyloxy)naphthalene;
2,3-diethoxy-1,4-di(phenylcarbamoyloxy)naphthalene;
2,3-diethoxy-1,4-di(benzylcarbamoyloxy)naphthalene;
2,3-di-n-propoxy-1,4-di(n-propylcarbamoyloxy)naphthalene;
2,3-di-n-propoxy-1,4-di(n-butylcarbamoyloxy)naphthalene;
2,3-di-n-propoxy-1,4-di(n-hexylcarbamoyloxy)naphthalene;
2,3-di-n-propoxy-1,4-di(cyclohexylcarbamoyloxy)naphthalene;
2,3-di-n-propoxy-1,4-di(phenylcarbamoyloxy)naphthalene;
2,3-diphenoxy-1,4-di(n-propylcarbamoyloxy)naphthalene;
2,3-diphenoxy-1,4-di(isopropylcarbamoyloxy)naphthalene;
2,3-diphenoxy-1,4-di(n-butylcarbamoyloxy)naphthalene;
2,3-diphenoxy-1,4-di(n-hexylcarbamoyloxy)naphthalene;
2,3-diphenoxy-1,4-di(2-methylhexylcarbamoyloxy)naphthalene;
2,3-diphenoxy-1,4-di(cyclohexylcarbamoyloxy)naphthalene;
2,3-diphenoxy-1,4-di(phenylcarbamoyloxy)naphthalene;
2,3-diphenoxy-1,4-di(benzylcarbamoyloxy)naphthalene;
2,3-dimethoxy-1,4-di(n-propylcarbamoyloxy)-6-chloronaphthalene;
2,3-dimethoxy-1,4-di(isopropylcarbamoyloxy)-6-chloronaphthalene;
2,3-dimethoxy-1,4-di(n-butylcarbamoyloxy)-6-chloronaphthalene;
2,3-dimethoxy-1,4-di(n-hexylcarbamoyloxy)-6-chloronaphthalene;
2,3-dimethoxy-1,4-di(2-methylhexylcarbamoyloxy)-6-chloronaphthalene;
2,3-dimethoxy-1,4-di(cyclohexylcarbamoyloxy)-6-chloronaphthalene;
2,3-dimethoxy-1,4-di(phenylcarbamoyloxy)-6-chloronaphthalene;
2,3-dimethoxy-1,4-di(benzylcarbamoyloxy)-6-chloronaphthalene;

2,3-diethoxy-1,4-di(n-propylcarbamoyloxy)-6-chloronaphthalene;
2,3-diethoxy-1,4-di(isopropylcarbamoyloxy)-6-methylnaphthalene;
2,3-diethoxy-1,4-di(n-butylcarbamoyloxy)-6-methoxynaphthalene;
2,3-diethoxy-1,4-di(n-hexylcarbamoyloxy)-6-fluoronaphthalene;
2,3-diethoxy-1,4-di(2-methylhexylcarbamoyloxy)-5,6-dimethylnaphthalene;
2,3-di-n-propoxy-1,4-di(cyclohexylcarbamoyloxy)-6-chloronaphthalene;
2,3-di-n-butoxy-1,4-di(phenylcarbamoyloxy)-6-chloronaphthalene;
2,3-diphenoxy-1,4-di(benzylcarbamoyloxy)-6-chloronaphthalene;
2-methoxy-3-methyl-1,4-di(ethylcarbamoyloxy)naphthalene;
2-methoxy-3-methyl-1,4-di(methylcarbamoyloxy)-6-chloronaphthalene;
2-methoxy-3-methyl-1,4-di(methylcarbamoyloxy)-7-bromonaphthalene;
2-methoxy-3-methyl-1,4-di(methylcarbamoyloxy)-6-fluoronaphthalene;
2-methoxy-3-methyl-1,4-di(methylcarbamoyloxy)-6-phenylnaphthalene;
2-methoxy-3-methyl-1,4-di(propylcarbamoyloxy)naphthalene;
2-methoxy-3-ethyl-1,4-di(ethylcarbamoyloxy)naphthalene;
2-methoxy-3-methyl-1,4-di(ethylcarbamoyloxy)-6-chloronaphthalene;
2-methoxy-3-methyl-1,4-di(ethylcarbamoyloxy)-7-bromonaphthalene;
2-methoxy-3-propyl-1,4-di(propylcarbamoyloxy)naphthalene;
2-methoxy-3-n-hexyl-1,4-di(methylcarbamoyloxy)naphthalene;
2-methoxy-3-phenyl-1,4-di(methylcarbamoyloxy)naphthalene;
2-methoxy-3-benzyl-1,4-di(methylcarbamoyloxy)naphthalene;
2-methoxy-3-t-butyl-1,4-di(methylcarbamoyloxy)naphthalene;
2-methoxy-3-methyl-1,4-di(methylcarbamoyloxy)-6-chloronaphthalene;
2-methoxy-1,4-di(n-propylcarbamoyloxy)naphthalene;
2-methoxy-1,4-di(isopropylcarbamoyloxy)naphthalene;
2-methoxy-1,4-di(n-butylcarbamoyloxy)naphthalene;
2-methoxy-1,4-di(n-hexylcarbamoyloxy)naphthalene;
2-methoxy-1,4-di(2-methylhexylcarbamoyloxy)naphthalene;
2-methoxy-1,4-di(cyclohexylcarbamoyloxy)naphthalene;
2-methoxy-1,4-di(phenylcarbamoyloxy)naphthalene;
2-methoxy-1,4-di(benzylcarbamoyloxy)naphthalene;
2-ethoxy-3-methyl-1,4-di(ethylcarbamoyloxy)naphthalene;
2-ethoxy-3-methyl-1,4-di(propylcarbamoyloxy)naphthalene;
2-ethoxy-3-ethyl-1,4-di(ethylcarbamoyloxy)naphthalene;
2-ethoxy-3-propyl-1,4-di(propylcarbamoyloxy)naphthalene;
2-ethoxy-3-n-hexyl-1,4-di(methylcarbamoyloxy)naphthalene;
2-ethoxy-3-phenyl-1,4-di(methylcarbamoyloxy)naphthalene;
2-ethoxy-3-methyl-1,4-di(methylcarbamoyloxy)-6-chloronaphthalene;
2-ethoxy-1,4-di(n-propylcarbamoyloxy)naphthalene;
2-ethoxy-1,4-di(isopropylcarbamoyloxy)naphthalene;
2-ethoxy-1,4-di(n-butylcarbamoyloxy)naphthalene;
2-ethoxy-1,4-di(n-hexylcarbamoyloxy)naphthalene;
2-ethoxy-1,4-di(2-methylhexylcarbamoyloxy)naphthalene;
2-ethoxy-1,4-di(cyclohexylcarbamoyloxy)naphthalene;
2-ethoxy-1,4-di(phenylcarbamoyloxy)naphthalene;
2-ethoxy-1,4-di(benzylcarbamoyloxy)naphthalene;
2-n-propoxy-1,4-di(n-propylcarbamoyloxy)naphthalene;
2-n-propoxy-1,4-di(n-butylcarbamoyloxy)naphthalene;
2-n-propoxy-1,4-di(n-hexylcarbamoyloxy)naphthalene;
2-n-propoxy-1,4-di(cyclohexylcarbamoyloxy)naphthalene;
2-n-propoxy-1,4-di(phenylcarbamoyloxy)naphthalene;
2-t-butoxy-1,4-di(methylcarbamoyloxy)naphthalene;
2-phenoxy-1,4-di(n-propylcarbamoyloxy)naphthalene;
2-phenoxy-1,4-di(isopropylcarbamoyloxy)naphthalene;
2-phenoxy-1,4-di(n-butylcarbamoyloxy)naphthalene;
2-phenoxy-1,4-di(n-hexylcarbamoyloxy)naphthalene;
2-phenoxy-1,4-di(2-methylhexylcarbamoyloxy)naphthalene;
2-phenoxy-1,4-di(cyclohexylcarbamoyloxy)naphthalene;
2-phenoxy-1,4-di(phenylcarbamoyloxy)naphthalene;
2-phenoxy-1,4-di(benzylcarbamoyloxy)naphthalene;
2-methoxy-1,4-di(n-propylcarbamoyloxy)-6-chloronaphthalene;
2-methoxy-1,4-di(isopropylcarbamoyloxy)-6-chloronaphthalene;
2-methoxy-1,4-di(n-butylcarbamoyloxy)-6-chloronaphthalene;
2-methoxy-1,4-di(n-hexylcarbamoyloxy)-6-chloronaphthalene;
2-methoxy-1,4-di(2-methylhexylcarbamoyloxy)-6-chloronaphthalene;
2-methoxy-1,4-di(cyclohexylcarbamoyloxy)-6-chloronaphthalene;
2-methoxy-1,4-di(phenylcarbamoyloxy)-6-chloronaphthalene;
2-methoxy-1,4-di(benzylcarbamoyloxy)-6-chloronaphthalene;
2-ethoxy-1,4-di(n-propylcarbamoyloxy)-6-chloronaphthalene;
2-ethoxy-1,4-di(isopropylcarbamoyloxy)-6-methylnaphthalene;
2-ethoxy-1,4-di(n-butylcarbamoyloxy)-6-methoxynaphthalene;
2-ethoxy-1,4-di(n-hexylcarbamoyloxy)-6-fluoronaphthalene;
2-ethoxy-1,4-di(2-methylhexylcarbamoyloxy)-5,6-dimethylnaphthalene;
2-n-propyl-1,4-di(cyclohexylcarbamoyloxy)-6-chloronaphthalene;
2-n-butoxy-1,4-di(phenylcarbamoyloxy)-6-chloronaphthalene; and
2-phenoxy-1,4-di(benzylcarbamoyloxy)-6-chloronaphthalene.

EXAMPLE 2

Preparation of 2,3-dimethoxy-1,4-bis(dimethylcarbamoyl oxy)naphthalene and related compounds of formula (Ia)

A. To a solution of 2.20 g of 2,3-dimethoxy-1,4-dihydroxynaphthalene, prepared as shown in Preparation 5, in 50 ml of dry benzene and 1.6 g of pyridine is added 16 ml of a solution of 12.5% phosgene in benzene. The mixture is stirred overnight at 25° C., filtered and the filtrate containing crude 2,3-dimethoxy-1,4-di(chlorocarbonyloxy)naphthalene is treated with a solution of 2.5 g of dimethylamine in 25 ml of tetrahydrofuran. After 4 hours at room temperature the reaction mixture is diluted with 250 ml of ethyl acetate, washed with dilute hydrochloric acid and dried over magnesium sulfate. The solvent is removed under reduced pressure and the residue chromatographed on silica gel giving 2,3-dimethoxy-1,4-bis(dimethylcarbamoyloxy)-naphthalene.

B. Similarly, following the procedure of paragraph A above, starting with the appropriate compound of formula (V) and the appropriate amine, the following compounds of formula (Ia) are prepared:

2,3-dimethoxy-1,4-di(methylcarbamoyloxy)naphthalene;
2,3-dimethoxy-1,4-di(ethylcarbamoyloxy)naphthalene;
2,3-dimethoxy-1,4-di(methylcarbamoyloxy)-6-chloronaphthalene;
2,3-dimethoxy-1,4-di(ethylcarbamoyloxy)-6-chloronaphthalene;
2,3-diphenoxy-1,4-di(methylcarbamoyloxy)naphthalene;
2-methoxy-1,4-di(methylcarbamoyloxy)naphthalene;
2-methoxy-3-methyl-1,4-di(methylcarbamoyloxy)naphthalene;
2,3-dimethoxy-1,4-di(ethylcarbamoyloxy)-6-fluoronaphthalene;
2,3-dimethoxy-1,4-di(methylcarbamoyloxy)-6,7-dimethylnaphthalene;
2,3-dimethoxy-1,4-di(n-propylcarbamoyloxy)naphthalene;
2,3-dimethoxy-1,4-di(n-hexylcarbamoyloxy)naphthalene;
2,3-dimethoxy-1,4-di(phenylcarbamoyloxy)naphthalene;
2,3-dimethoxy-1,4-di(benzylcarbamoyloxy)naphthalene;
2,3-dimethoxy-1,4-di(carbamoyloxy)naphthalene;
2,3-dimethoxy-1,4-bis(diethylcarbamoyloxy)naphthalene;
2,3-dimethoxy-1,4-bis(di-n-hexylcarbamoyloxy)naphthalene;
2,3-dimethoxy-1,4-di(N-methyl-N-hexylcarbamoyloxy)naphthalene;
2,3-dimethoxy-1,4-di(N-methyl-N-phenylcarbamoyloxy)naphthalene;
2,3-dimethoxy-1,4-di(N-methyl-N-cyclopentylcarbamoyloxy)naphthalene;
2,3-diethoxy-1,4-di(methylcarbamoyloxy)-6-chloronaphthalene;
2,3-diethoxy-1,4-di(methylcarbamoyloxy)-6,7-dimethylnaphthalene;
2,3-diethoxy-1,4-di(n-hexylcarbamoyloxy)naphthalene;
2,3-diethoxy-1,4-di(cyclohexylcarbamoyloxy)naphthalene;
2,3-diethoxy-1,4-bis(diethylcarbamoyloxy)naphthalene;
2,3-diethoxy-1,4-bis(di-n-hexylcarbamoyloxy)naphthalene;
2,3-diethoxy-1,4-di(N-methyl-N-hexylcarbamoyloxy)naphthalene;
2,3-diethoxy-1,4-di(N-methyl-N-phenylcarbamoyloxy)naphthalene;
2,3-di-n-propoxy-1,4-di(methylcarbamoyloxy)naphthalene;
2,3-di-n-propoxy-1,4-bis(dimethylcarbamoyloxy)naphthalene;
2-methoxy-3-methyl-1,4-di(methylcarbamoyloxy)-6-chloronaphthalene;
2-methoxy-3-methyl-1,4-bis(dimethylcarbamoyloxy)naphthalene;
2-methoxy-3-methyl-1,4-di(methylcarbamoyloxy)-7-chloronaphthalene;
2-methoxy-3-methyl-1,4-di(N-methyl-N-hexylcarbamoyloxy)naphthalene;
2-methoxy-3-methyl-1,4-di(ethylcarbamoyloxy)naphthalene;
2-methoxy-3-methyl-1,4-di(propylcarbamoyloxy)naphthalene;
2-methoxy-3-ethyl-1,4-bis(diethylcarbamoyloxy)naphthalene;
2-methoxy-3-methyl-1,4-di(ethylcarbamoyloxy)-6-chloronaphthalene;
2-methoxy-3-n-hexyl-1,4-di(methylcarbamoyloxy)naphthalene;
2-methoxy-1,4-di(n-propylcarbamoyloxy)naphthalene;
2-methoxy-1,4-bis(dimethylcarbamoyloxy)naphthalene;
2-methoxy-1,4-di(N-methyl-N-butylcarbamoyloxy)naphthalene;
2-methoxy-1,4-di(n-hexylcarbamoyloxy)naphthalene;
2-methoxy-1,4-di(N-ethyl-N-hexylcarbamoyloxy)naphthalene;
2-methoxy-1,4-bis(dicyclohexylcarbamoyloxy)naphthalene;
2-ethoxy-1,4-di(n-propylcarbamoyloxy)naphthalene;
2-ethoxy-1,4-bis(dimethylcarbamoyloxy)naphthalene;
2-n-propoxy-1,4-di(N-methyl-N-butylcarbamoyloxy)naphthalene;
2-n-hexyloxy-1,4-di(n-hexylcarbamoyloxy)naphthalene;
2-methoxy-1,4-di(N-ethyl-N-hexylcarbamoyloxy)-6-chloronaphthalene; and
2-methoxy-3-n-hexyl-1,4-bis(dicyclohexylcarbamoyloxy)naphthalene.

EXAMPLE 3

Preparation of 2,3-dimethoxy-1,4-di(methoxycarbonyloxy)naphthalene and related Compounds of Formula (Ib)

A. To a solution of 1.0 g of 2,3-dimethoxy-1,4-dihydroxynaphthalene, prepared as shown in Preparation 5, in 50 ml of tetrahydrofuran was added 1.40 g of methyl chloroformate followed by 1.50 g of triethylamine. The mixture was stirred at room temperature for 16 hours, filtered, then the solvent removed under reduced pressure. The residue was dissolved in diethyl ether, washed with dilute hydrochloric acid and dried over anhydrous sodium sulfate. The ether was removed under reduced pressure and the residue chromatographed on silica gel, eluting with a 1:1 mixture of methylene chloride and hexane, to give 2,3-dimethoxy-1,4-di(methoxycarbonyloxy)naphthalene, m.p. 53°-54° C.

B. Similarly, starting with the appropriate compound of formula (V) and the appropriate chloroformate of formula ClC(O)OR$^4$, the following compounds of formula (Ib) were prepared:

2,3-dimethoxy-1,4-di(methoxycarbonyloxy)-6-chloronaphthalene, m.p. 115°–116° C.
2,3-dimethoxy-1,4-di(ethoxycarbonyloxy)naphthalene, m.p. 94°–95° C.
2,3-dimethoxy-1,4-di(ethoxycarbonyloxy)-6-chloronaphthalene, m.p. 94°–95° C.
2,3-dimethoxy-1,4-di(phenoxycarbonyloxy)-6-chloronaphthalene, m.p. 199°–200° C.
2,3-diphenoxy-1,4-di(methoxycarbonyloxy)naphthalene, m.p. 124°–125° C.
2,3-diphenoxy-1,4-di(methoxycarbonyloxy)-6-chloronaphthalene, m.p. 106°–107° C.
2-methoxy-1,4-di(methoxycarbonyloxy)naphthalene, m.p. 118°–119° C.
2-methoxy-3-methyl-1,4-di(methoxycarbonyloxy)naphthalene, m.p. 86°–87° C.

C. Similarly, optionally replacing 2,3-dimethoxy-1,4-dihydroxynaphthalene with other compounds of formula (V), prepared as shown in Preparation 5, and optionally replacing methyl chloroformate with an appropriately substituted chloroformate of formula ClC(O)OR$^4$ or an appropriately substituted dicarbonate of formula R$^4$OC(O)OC(O)OR$^4$, the following compounds of formula (Ib) are prepared:

2,3-dimethoxy-1,4-di(ethoxycarbonyloxy)naphthalene;
2,3-dimethoxy-1,4-di(methoxycarbonyloxy)-6-chloronaphthalene;
2,3-dimethoxy-1,4-di(methoxycarbonyloxy)-6-fluoronaphthalene;
2,3-dimethoxy-1,4-di(methoxycarbonyloxy)-6-phenylnaphthalene;
2,3-dimethoxy-1,4-di(methoxycarbonyloxy)-6,7-dimethylnaphthalene;
2,3-dimethoxy-1,4-di(n-propoxycarbonyloxy)naphthalene;
2,3-dimethoxy-1,4-di(isopropoxycarbonyloxy)naphthalene;
2,3-dimethoxy-1,4-di(n-butoxycarbonyloxy)naphthalene;
2,3-dimethoxy-1,4-di(n-hexyloxycarbonyloxy)naphthalene;
2,3-dimethoxy-1,4-di(2-methylhexyloxycarbonyloxy)naphthalene;
2,3-dimethoxy-1,4-di(cyclohexyloxycarbonyloxy)naphthalene;
2,3-dimethoxy-1,4-di(phenoxycarbonyloxy)naphthalene;
2,3-dimethoxy-1,4-di(benzyloxycarbonyloxy)naphthalene;
2,3-diethoxy-1,4-di(methoxycarbonyloxy)-6-chloronaphthalene;
2,3-diethoxy-1,4-di(methoxycarbonyloxy)-6-fluoronaphthalene;
2,3-diethoxy-1,4-di(methoxycarbonyloxy)-6-phenylnaphthalene;
2,3-diethoxy-1,4-di(methoxycarbonyloxy)-6,7-dimethylnaphthalene;
2,3-diethoxy-1,4-di(n-propoxycarbonyloxy)naphthalene;
2,3-diethoxy-1,4-di(isopropoxycarbonyloxy)naphthalene;
2,3-diethoxy-1,4-di(n-butoxycarbonyloxy)naphthalene;
2,3-diethoxy-1,4-di(n-hexyloxycarbonyloxy)naphthalene;
2,3-diethoxy-1,4-di(2-methylhexyloxycarbonyloxy)naphthalene;
2,3-diethoxy-1,4-di(cyclohexyloxycarbonyloxy)naphthalene;
2,3-diethoxy-1,4-di(phenoxycarbonyloxy)naphthalene;
2,3-diethoxy-1,4-di(benzyloxycarbonyloxy)naphthalene;
2,3-di-n-propoxy-1,4-di(n-propoxycarbonyloxy)naphthalene;
2,3-di-n-propoxy-1,4-di(n-butoxycarbonyloxy)naphthalene;
2,3-di-n-propoxy-1,4-di(n-hexyloxycarbonyloxy)naphthalene;
2,3-di-n-propoxy-1,4-di(cyclohexyloxycarbonyloxy)naphthalene;
2,3-di-n-propoxy-1,4-di(phenoxycarbonyloxy)naphthalene;
2,3-diphenoxy-1,4-di(n-propoxycarbonyloxy)naphthalene;
2,3-diphenoxy-1,4-di(isopropoxycarbonyloxy)naphthalene;
2,3-diphenoxy-1,4-di(n-butoxycarbonyloxy)naphthalene;
2,3-diphenoxy-1,4-di(n-hexyloxycarbonyloxy)naphthalene;
2,3-diphenoxy-1,4-di(2-methylhexyloxycarbonyloxy)naphthalene;
2,3-diphenoxy-1,4-di(cyclohexyloxycarbonyloxy)naphthalene;
2,3-diphenoxy-1,4-di(phenoxycarbonyloxy)naphthalene;
2,3-diphenoxy-1,4-di(benzyloxycarbonyloxy)naphthalene;
2,3-dimethoxy-1,4-di(n-propoxycarbonyloxy)-6-chloronaphthalene;
2,3-dimethoxy-1,4-di(isopropoxycarbonyloxy)-6-chloronaphthalene;
2,3-dimethoxy-1,4-di(n-butoxycarbonyloxy)-6-chloronaphthalene;
2,3-dimethoxy-1,4-di(n-hexyloxycarbonyloxy)-6-chloronaphthalene;
2,3-dimethoxy-1,4-di(2-methylhexyloxycarbonyloxy)-6-chloronaphthalene;
2,3-dimethoxy-1,4-di(cyclohexyloxycarbonyloxy)-6-chloronaphthalene;
2,3-dimethoxy-1,4-di(phenoxycarbonyloxy)-6-chloronaphthalene;
2,3-dimethoxy-1,4-di(benzyloxycarbonyloxy)-6-chloronaphthalene;
2,3-diethoxy-1,4-di(n-propoxycarbonyloxy)-6-chloronaphthalene;
2,3-diethoxy-1,4-di(isopropoxycarbonyloxy)-6-methylnaphthalene;
2,3-diethoxy-1,4-di(n-butoxycarbonyloxy)-6-methoxynaphthalene;
2,3-diethoxy-1,4-di(n-hexyloxycarbonyloxy)-6-fluoronaphthalene;
2,3-diethoxy-1,4-di(2-methylhexyloxycarbonyloxy)-5,6-dimethylnaphthalene;
2,3-di-n-propoxy-1,4-di(cyclohexyloxycarbonyloxy)-6-chloronaphthalene;
2,3-di-n-butoxy-1,4-di(phenoxycarbonyloxy)-6-chloronaphthalene;
2,3-diphenoxy-1,4-di(benzyloxycarbonyloxy)-6-chloronaphthalene;
2-methoxy-3-methyl-1,4-di(ethoxycarbonyloxy)naphthalene;
2-methoxy-3-methyl-1,4-di(propoxycarbonyloxy)naphthalene;

2-methoxy-3-ethyl-1,4-di(ethoxycarbonyloxy)naphthalene;
2-methoxy-3-propyl-1,4-di(propoxycarbonyloxy)naphthalene;
2-methoxy-3-t-butyl-1,4-di(methoxycarbonyloxy)naphthalene;
2-methoxy-3-n-hexyl-1,4-di(methoxycarbonyloxy)naphthalene;
2-methoxy-3-phenyl-1,4-di(methoxycarbonyloxy)naphthalene;
2-methoxy-3-benzyl-1,4-di(methoxycarbonyloxy)naphthalene;
2-methoxy-3-methyl-1,4-di(methoxycarbonyloxy)-6-chloronaphthalene;
2-methoxy-1,4-di(n-propoxycarbonyloxy)naphthalene;
2-methoxy-1,4-di(isopropoxycarbonyloxy)naphthalene;
2-methoxy-1,4-di(n-butoxycarbonyloxy)naphthalene;
2-methoxy-1,4-di(n-hexyloxycarbonyloxy)naphthalene;
2-methoxy-1,4-di(2-methylhexyloxycarbonyloxy)naphthalene;
2-methoxy-1,4-di(cyclohexyloxycarbonyloxy)naphthalene;
2-methoxy-1,4-di(phenoxycarbonyloxy)naphthalene;
2-methoxy-1,4-di(benzyloxycarbonyloxy)naphthalene;
2-ethoxy-3-methyl-1,4-di(ethoxycarbonyloxy)naphthalene;
2-ethoxy-3-methyl-1,4-di(propoxycarbonyloxy)naphthalene;
2-ethoxy-3-ethyl-1,4-di(ethoxycarbonyloxy)naphthalene;
2-ethoxy-3-propyl-1,4-di(propoxycarbonyloxy)naphthalene;
2-ethoxy-3-n-hexyl-1,4-di(methoxycarbonyloxy)naphthalene;
2-ethoxy-3-phenyl-1,4-di(methoxycarbonyloxy)naphthalene;
2-ethoxy-3-methyl-1,4-di(methoxycarbonyloxy)-6-chloronaphthalene;
2-ethoxy-1,4-di(n-propoxycarbonyloxy)naphthalene;
2-ethoxy-1,4-di(isopropoxycarbonyloxy)naphthalene;
2-ethoxy-1,4-di(n-butoxycarbonyloxy)naphthalene;
2-ethoxy-1,4-di(n-hexyloxycarbonyloxy)naphthalene;
2-ethoxy-1,4-di(2-methylhexyloxycarbonyloxy)naphthalene;
2-ethoxy-1,4-di(cyclohexoxycarbonyloxy)naphthalene;
2-ethoxy-1,4-di(phenoxycarbonyloxy)naphthalene;
2-ethoxy-1,4-di(benzyloxycarbonyloxy)naphthalene;
2-n-propoxy-1,4-di(n-propoxycarbonyloxy)naphthalene;
2-n-propoxy-1,4-di(n-butoxycarbonyloxy)naphthalene;
2-n-propoxy-1,4-di(n-hexyloxycarbonyloxy)naphthalene;
2-n-propoxy-1,4-di(cyclohexyloxycarbonyloxy)naphthalene;
2-n-propoxy-1,4-di(phenoxycarbonyloxy)naphthalene;
2-t-butoxy-1,4-di(methoxycarbonyloxy)naphthalene;
2-phenoxy-1,4-di(n-propoxycarbonyloxy)naphthalene;
2-phenoxy-1,4-di(isopropoxycarbonyloxy)naphthalene;
2-phenoxy-1,4-di(n-butoxycarbonyloxy)naphthalene;
2-phenoxy-1,4-di(n-hexyloxycarbonyloxy)naphthalene;
2-phenoxy-1,4-di(2-methylhexyloxycarbonyloxy)naphthalene;
2-phenoxy-1,4-di(cyclohexyloxycarbonyloxy)naphthalene;
2-phenoxy-1,4-di(phenoxycarbonyloxy)naphthalene;
2-phenoxy-1,4-di(benzyloxycarbonyloxy)naphthalene;
2-methoxy-1,4-di(n-propoxycarbonyloxy)-6-chloronaphthalene;
2-methoxy-1,4-di(isopropoxycarbonyloxy)-6-chloronaphthalene;
2-methoxy-1,4-di(n-butoxycarbonyloxy)-6-chloronaphthalene;
2-methoxy-1,4-di(n-hexyloxycarbonyloxy)-6-chloronaphthalene;
2-methoxy-1,4-di(2-methylhexyloxycarbonyloxy)-6-chloronaphthalene;
2-methoxy-1,4-di(cyclohexyloxycarbonyloxy)-6-chloronaphthalene;
2-methoxy-1,4-di(phenoxycarbonyloxy)-6-chloronaphthalene;
2-methoxy-1,4-di(benzyloxycarbonyloxy)-6-chloronaphthalene;
2-ethoxy-1,4-di(n-propoxycarbonyloxy)-6-chloronaphthalene;
2-ethoxy-1,4-di(isopropoxycarbonyloxy)-6-methylnaphthalene;
2-ethoxy-1,4-di(n-butoxycarbonyloxy)-6-methoxynaphthalene;
2-ethoxy-1,4-di(n-hexyloxycarbonyloxy)-6-fluoronaphthalene;
2-ethoxy-1,4-di(2-methylhexyloxycarbonyloxy)-5,6-dimethylnaphthalene;
2-n-propoxy-1,4-di(cyclohexyloxycarbonyloxy)-6-chloronaphthalene;
2-n-butoxy-1,4-di(phenoxycarbonyloxy)-6-chloronaphthalene; and
2-phenoxy-1,4-di(benzyloxycarbonyloxy)-6-chloronaphthalene.

What is claimed is:
1. A compound of the formula

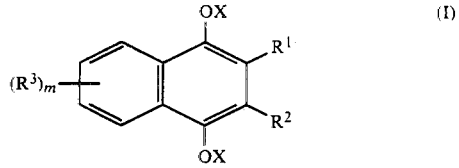

wherein:
R$^1$ is lower alkoxy of one to six carbon atoms or phenoxy optionally substituted by one or two substituents chosen from lower alkyl of one to four carbon atoms, lower alkoxy of one to four carbon atoms and halo;

R$^2$ is the same as R$^1$, or R$^2$ is hydrogen, lower alkyl of one to six carbon atoms, phenyl or phenyl-lower-alkyl, wherein the phenyl ring of the phenyl or phenyl-lower-alkyl group is optionally substituted by one or two substituents chosen from lower alkyl of one to four carbon atoms, lower alkoxy of one to four carbon atoms and halo;

R$^3$ is hydrogen, halo, lower alkyl of one to six carbon atoms, lower alkoxy of one to six carbon atoms, phenyl, phenyl-lower-alkyl or phenyl-lower-alkoxy, wherein the phenyl ring of the phenyl, phenyl-lower-alkyl or phenyl-lower-alkoxy group is optionally substituted by one or two substituents chosen from lower alkyl of one to four carbon atoms, lower alkoxy of one to four carbon atoms and halo;

m is 1 or 2; and both X groups are the same and X is —C(O)OR$^4$ or —C(O)NR$^5$R$^6$, wherein R$^4$ is alkyl of one or seven carbon atoms, phenyl or benzyl, wherein the phenyl ring of the phenyl or benzyl group is optionally substituted by one or two substituents chosen from lower alkyl of one to four carbon atoms, lower alkoxy of one to four carbon atoms and halo; and $R^5$ and $R^6$ are independently hydrogen, lower alkyl of one to six carbon atoms, cycloalkyl of five to eight carbon atoms or phenyl optionally substituted with one or two substituents chosen from lower alkyl of one to four carbon atoms, lower alkoxy of one to four carbon atoms and halo.

2. The compound of claim 1, wherein X is —C(O)OR$^4$.

3. The compound of claim 2, wherein $R^1$ and $R^2$ are the same and are methoxy, ethoxy, n-propoxy or phenoxy.

4. The compound of claim 3, wherein $R^4$ is methyl, ethyl, n-propyl or phenyl.

5. The compound of claim 4, wherein $R^3$ is hydrogen or chloro.

6. The compound of claim 5, wherein $R^1$ and $R^2$ are both methoxy, $R^3$ is hydrogen and $R^4$ is methyl, namely 2,3-dimethoxy-1,4-di(methoxycarbonyloxy)naphthalene.

7. The compound of claim 5, wherein $R^1$ and $R^2$ are both methoxy, $R^3$ is hydrogen and $R^4$ is ethyl, namely 2,3-dimethoxy-1,4-di(ethoxycarbonyloxy)naphthalene.

8. The compound of claim 5, wherein $R^1$ and $R^2$ are both phenoxy, $R^3$ is hydrogen and $R^4$ is methyl, namely 2,3-diphenoxy-1,4-di(methoxycarbonyloxy)naphthalene.

9. The compound of claim 5, wherein $R^1$ and $R^2$ are both methoxy, $R^3$ is 6-chloro and $R^4$ is methyl, namely 2,3-dimethoxy-1,4-di(methoxycarbonyloxy)-6-chloronaphthalene.

10. The compound of claim 5, wherein $R^1$ and $R^2$ are both methoxy, $R^3$ is 6-chloro and $R^4$ is ethyl, namely 2,3-dimethoxy-1,4-di(ethoxycarbonyloxy)-6-chloronaphthalene.

11. The compound of claim 5, wherein $R^1$ and $R^2$ are both methoxy, $R^3$ is 6-chloro and $R^4$ is phenyl, namely 2,3-dimethoxy-1,4-di(phenoxycarbonyloxy)-6-chloronaphthalene.

12. The compound of claim 2, wherein $R^1$ is lower alkoxy of one to six carbon atoms or optionally substituted phenoxy and $R^2$ is hydrogen, lower alkyl of one to six carbon atoms, optionally substituted phenyl or optionally substituted phenylalkyl.

13. The compound of claim 12, wherein $R^1$ is methoxy, ethoxy, n-propoxy or phenoxy.

14. The compound of claim 13, wherein $R^2$ is hydrogen, methyl, ethyl or n-propyl.

15. The compound of claim 14, wherein $R^4$ is methyl, ethyl or n-propyl.

16. The compound of claim 15, wherein $R^3$ is hydrogen or chloro.

17. The compound of claim 16, wherein $R^1$ is methoxy, $R^2$ and $R^3$ are both hydrogen and $R^4$ is methyl, namely 2-methoxy-1,4-di(methoxycarbonyloxy)naphthalene.

18. The compound of claim 16, wherein $R^1$ is methoxy, $R^2$ is methyl, $R^3$ is hydrogen and $R^4$ is methyl, namely 2-methoxy-3-methyl-1,4-di(methoxycarbonyloxy)naphthalene.

19. The compound of claim 1, wherein X is —C(O)NR$^5$R$^6$.

20. The compound of claim 19, wherein $R^1$ and $R^2$ are the same and are methoxy, ethoxy, n-propoxy or phenoxy.

21. The compound of claim 20, wherein $R^5$ and $R^6$ are independently hydrogen, methyl, ethyl, n-propyl or phenyl.

22. The compound of claim 21, wherein $R^3$ is hydrogen or chloro.

23. The compound of claim 22, wherein $R^1$ and $R^2$ are both methoxy, $R^3$ and $R^5$ are both hydrogen and $R^6$ is methyl, namely 2,3-dimethoxy-1,4-di(methylcarbamoyloxy)naphthalene.

24. The compound of claim 22, wherein $R^1$ and $R^2$ are both methoxy, $R^3$ and $R^5$ are both hydrogen and $R^6$ is ethyl, namely, 2,3-dimethoxy-1,4-di(ethylcarbamoyloxy)naphthalene.

25. The compound of claim 22, wherein $R^1$ and $R^2$ are both phenoxy, $R^3$ and $R^5$ are both hydrogen and $R^6$ is methyl, namely 2,3-diphenoxy-1,4-di(methylcarbamoyloxy)naphthalene.

26. The compound of claim 22, wherein $R^1$ and $R^2$ are both methoxy, $R^3$ is 6-chloro, $R^5$ is hydrogen and $R^6$ is methyl, namely 2,3-dimethoxy-1,4-di(methylcarbamoyloxy)-6-chloronaphthalene.

27. The compound of claim 22, wherein $R^1$ and $R^2$ are both methoxy, $R^3$ is 6-chloro, $R^5$ is hydrogen and $R^6$ is ethyl, namely 2,3-dimethoxy-1,4-di(ethylcarbamoyloxy)-6-chloronaphthalene.

28. The compound of claim 19, wherein $R^1$ is lower alkoxy of one to six carbon atoms or optionally substituted phenoxy and $R^2$ is hydrogen, lower alkyl of one to six carbon atoms, optionally substituted phenyl or optionally substituted phenylalkyl.

29. The compound of claim 28, wherein $R^1$ is methoxy, ethoxy, n-propoxy or phenoxy.

30. The compound of claim 29, wherein $R^2$ is hydrogen, methyl, ethyl or n-propyl.

31. The compound of claim 30, wherein $R^5$ and $R^6$ are independently hydrogen, methyl, ethyl, n-propyl or phenyl.

32. The compound of claim 31, wherein $R^3$ is hydrogen or chloro.

33. The compound of claim 32, wherein $R^1$ is methoxy, $R^2$, $R^3$ and $R^5$ are each hydrogen and $R^6$ is methyl, namely 2-methoxy-1,4-di(methylcarbamoyloxy)naphthalene.

34. The compound of claim 32, wherein $R^1$ is methoxy, $R^2$ is methyl, $R^3$ and $R^5$ are both hydrogen and $R^6$ is methyl, namely 2-methoxy-3-methyl-1,4-di(methylcarbamoyloxy)naphthalene.

35. A composition in a form suitable for topical administration for treating the condition of psoriasis which composition comprises a pharmaceutically acceptable, non-toxic carrier and a psoriasis relieving amount of a compound of the formula

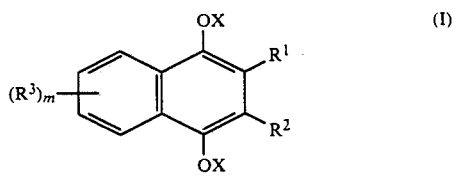

wherein:
$R^1$ is lower alkoxy of one to six carbon atoms or phenoxy optionally substituted by one or two substituents chosen from lower alkyl of one to four carbon atoms, lower alkoxy of one to four carbon atoms and halo;

$R^2$ is the same as $R^1$, or $R^2$ is hydrogen, lower alkyl of one to six carbon atoms, phenyl or phenyl-lower-alkyl, wherein the phenyl ring of the phenyl or phenyl-lower-alkyl group is optionally substituted by one or two substituents chosen from lower alkyl of one to four carbon atoms, lower alkoxy of one to four carbon atoms and halo;

$R^3$ is hydrogen, halo, lower alkyl of one to six carbon atoms, lower alkoxy of one to six carbon atoms, phenyl, phenyl-lower-alkyl or phenyl-lower-alkoxy, wherein the phenyl ring of the phenyl, phenyl-lower-alkyl or phenyl-lower-alkoxy group is optionally substituted by one to two substituents chosen from lower alkyl of one to four carbon atoms, lower alkoxy of one to four carbon atoms and halo;

m is 1 or 2; and both X groups are the same and X is —C(O)OR$^4$ or —C(O)NR$^5$R$^6$, wherein $R^4$ is alkyl of one to seven carbon atoms, phenyl or benzyl, wherein the phenyl ring of the phenyl or benzyl group is optionally substituted by one or two substituents chosen from lower alkyl of one to four carbon atoms, lower alkoxy of one to four carbon atoms and halo; and $R^5$ and $R^6$ are independently hydrogen, lower alkyl of one to six carbon atoms, cycloalkyl of five to eight carbon atoms or phenyl optionally substituted with one or two substituents chosen from lower alkyl of one to four carbon atoms, lower alkoxy of one to four carbon atoms and halo.

36. A method of treating psoriasis in mammals which comprises applying an effective amount of a compound of the formula

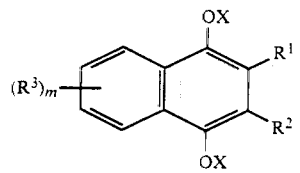

wherein:

$R^1$ is lower alkoxy of one to six carbon atoms or phenoxy optionally substituted by one or two substituents chosen from lower alkyl of one to four carbon atoms, lower alkoxy of one to four carbon atoms and halo;

$R^2$ is the same as $R^1$, or $R^2$ is hydrogen, lower alkyl of one to six carbon atoms, phenyl or phenyl-lower-alkyl, wherein the phenyl ring of the phenyl or phenyl-lower-alkyl group is optionally substituted by one or two substituents chosen from lower alkyl of one to four carbon atoms, lower alkoxy of one to four carbon atoms and halo;

$R^3$ is hydrogen, halo, lower alkyl of one to six carbon atoms, lower alkoxy of one to six carbon atoms, phenyl, phenyl-lower-alkyl or phenyl-lower-alkoxy, wherein the phenyl ring of the phenyl, phenyl-lower-alkyl or phenyl-lower-alkoxy group is optionally substituted by one or two substituents chosen from lower alkyl of one to four carbon atoms, lower alkoxy of one to four carbon atoms and halo;

m is 1 or 2; and both X groups are the same and X is —C(O)OR$^4$ or —C(O)NR$^5$R$^6$, wherein $R^4$ is alkyl of one to seven carbon atoms, phenyl or benzyl, wherein the phenyl ring of the phenyl or benzyl group is optionally substituted by one or two substituents chosen from lower alkyl of one to four carbon atoms, lower alkoxy of one to four carbon atoms and halo; and $R^5$ and $R^6$ are independently hydrogen, lower alkyl of one to six carbon atoms, cycloalkyl of five to eight carbon atoms or phenyl optionally substituted with one or two substituents chosen from lower alkyl of one to four carbon atoms, lower alkoxy of one to four carbon atoms and halo.

* * * * *